US012730088B2

(12) United States Patent
Lim et al.

(10) Patent No.: US 12,730,088 B2
(45) Date of Patent: Sep. 8, 2026

(54) BIOSENSOR CARTRIDGE AND BIOSENSOR SYSTEM INCLUDING SAME

(71) Applicant: LG ELECTRONICS INC., Seoul (KR)

(72) Inventors: Kyoungtaek Lim, Seoul (KR); Youngrae Lee, Seoul (KR); Seonggeun Kim, Seoul (KR); Younghwan Kim, Seoul (KR); Changseok Kim, Seoul (KR); Kyungho Kong, Seoul (KR); Kyounghwa Kim, Seoul (KR); Taekyu Choi, Seoul (KR); Inkwan Yeo, Seoul (KR)

(73) Assignee: LG ELECTRONICS INC., Seoul (KR)

( * ) Notice: Subject to any disclaimer, the term of this patent is extended or adjusted under 35 U.S.C. 154(b) by 803 days.

(21) Appl. No.: 17/993,351

(22) Filed: Nov. 23, 2022

(65) Prior Publication Data

US 2023/0330661 A1 Oct. 19, 2023

(30) Foreign Application Priority Data

Apr. 19, 2022 (KR) ........................ 10-2022-0047913

(51) Int. Cl.

*G01N 27/414* (2006.01)
*A61B 5/05* (2021.01)
*A61B 10/00* (2006.01)
*G01N 33/487* (2006.01)
*G01N 33/543* (2006.01)

(52) U.S. Cl.

CPC ........... *G01N 27/4145* (2013.01); *A61B 5/05* (2013.01); *A61B 10/0045* (2013.01); *G01N 27/414* (2013.01); *G01N 33/48785* (2013.01); *G01N 33/5438* (2013.01); *B01L 2200/027* (2013.01); *B01L 2300/0636* (2013.01); *B01L 2300/0645* (2013.01); *B01L 2300/0663* (2013.01); *H01R 2201/20* (2013.01); *H05K 2201/10151* (2013.01)

(58) Field of Classification Search

CPC ............. G01N 27/4145; G01N 27/414; G01N 33/48785; G01N 33/5438; G01N 33/48707; G01N 33/48771; G01N 33/48778; G01N 33/48792; G01N 27/4146; A61B 5/05; A61B 10/0045; A61B 5/0077; A61B 5/14546; A61B 5/1468; A61B 5/1486; A61B 5/4887; A61B 5/0002; A61B 5/061; A61B 2562/08; B01L 2200/027; B01L 2300/0636; B01L 2300/0645; B01L 2300/0663; B01L 3/502715; H01R 2201/20; H01R 13/465; H01R 13/6683; H01R 2201/12; H01R 12/72; H05K 2201/10151; H05K 2201/10265; H05K 1/181; H05K 2201/10166; H05K 2201/10386; G06K 7/1417; G06K 7/1447; G06Q 20/3223

See application file for complete search history.

(56) References Cited

U.S. PATENT DOCUMENTS

| | | | | |
|---|---|---|---|---|
| 9,805,165 | B2 | 10/2017 | Xiang et al. | |
| 11,342,051 | B1 | 5/2022 | Jain et al. | |
| 12,455,258 | B2 | 10/2025 | Kim et al. | |
| 2004/0244151 | A1 | 12/2004 | Sakata et al. | |
| 2008/0280285 | A1 * | 11/2008 | Chen ................ | G01N 35/00029 436/86 |
| 2009/0124876 | A1 | 5/2009 | Nakamura et al. | |
| 2014/0052475 | A1 | 2/2014 | Madan et al. | |
| 2014/0273187 | A1 | 9/2014 | Johnson et al. | |
| 2014/0308459 | A1 * | 10/2014 | Miyazaki ........... | G01N 27/3272 427/125 |
| 2015/0083589 | A1 * | 3/2015 | Lee ...................... | G01N 27/327 204/403.01 |
| 2015/0268186 | A1 | 9/2015 | Pagels | |

(Continued)

FOREIGN PATENT DOCUMENTS

| | | | |
|---|---|---|---|
| CA | 3175822 | A1 | 10/2021 |
| JP | 2000-258493 | A | 9/2000 |

(Continued)

OTHER PUBLICATIONS

US 12,429,455 B2, 09/2025, Kim (withdrawn)*

Sommers A, Panth M, Eid K. "Self-propelled water droplet movement on a laser-etched radial gradient copper surface." Applied Thermal Engineering 173 (2020) 115226 (Year: 2020).*

Cheah et al., "Integrated Platform Addressing the Finger-Prick Blood Processing Challenges of Point-of-Care Electrical Biomarker Testing", Analytical Chemistry, vol. 94, No. 1, published Jan. 3, 2022, pp. 1256-1263.

(Continued)

*Primary Examiner* — Lyle Alexander
*Assistant Examiner* — Alison Claire Gerhard
(74) *Attorney, Agent, or Firm* — Birch. Stewart, Kolasch & Birch, LLP

(57) ABSTRACT

A biosensor cartridge can include a circuit board including a connection terminal electrically connectable to an external diagnostic device; a sensor chip detecting a target material from an applied analysis specimen, having a reactant reacting specifically with the target material, and transmitting an electrical signal generated by reacting with the detected target material to the connection terminal of the circuit board; and a housing accommodating the circuit board and the sensor chip and surround the circuit board and the sensor chip so that the connection terminal is exposed. The housing has an inclined surface dent from an upper surface and forms an accommodating portion that exposes the sensor area of the sensor chip and accommodates the test specimen. Further, the accommodating portion includes a pattern structure for lowering surface energy.

20 Claims, 17 Drawing Sheets

(56) References Cited

U.S. PATENT DOCUMENTS

| | | | |
|---|---|---|---|
| 2015/0352550 | A1* | 12/2015 | Bhargava .......... B01L 3/502746 436/164 |
| 2016/0084793 | A1 | 3/2016 | Chen et al. |
| 2018/0272342 | A1* | 9/2018 | Samsoondar ..... B01L 3/502784 |
| 2019/0041355 | A1 | 2/2019 | Merriman et al. |
| 2019/0234907 | A1* | 8/2019 | Edwards ................ G01N 29/22 |
| 2020/0108385 | A1 | 4/2020 | Temiz et al. |
| 2020/0170552 | A1 | 6/2020 | Cho et al. |
| 2020/0333286 | A1 | 10/2020 | Leon et al. |
| 2021/0003528 | A1 | 1/2021 | Esquivel-Upshaw et al. |
| 2021/0129133 | A1 | 5/2021 | Ohta et al. |
| 2021/0285977 | A1 | 9/2021 | Tu et al. |
| 2021/0365445 | A1 | 11/2021 | Robell et al. |

FOREIGN PATENT DOCUMENTS

| | | | | |
|---|---|---|---|---|
| JP | 2003-149192 | A | 5/2003 | |
| JP | 2008-46094 | A | 2/2008 | |
| JP | 2013-83506 | A | 5/2013 | |
| JP | 2020-126077 | A | 8/2020 | |
| KR | 20-0311804 | Y1 | 5/2003 | |
| KR | 10-0813398 | B1 | 3/2008 | |
| KR | 10-2008-0110356 | A | 12/2008 | |
| KR | 10-2010-0072533 | A | 7/2010 | |
| KR | 10-2010-0103932 | A | 9/2010 | |
| KR | 10-2011-0064754 | A | 6/2011 | |
| KR | 10-2012-0101806 | A | 9/2012 | |
| KR | 10-2013-0012744 | A | 2/2013 | |
| KR | 10-1323373 | B1 | 10/2013 | |
| KR | 10-2014-0120138 | A | 10/2014 | |
| KR | 10-1507317 | B1 | 3/2015 | |
| KR | 10-2016-0017684 | A | 2/2016 | |
| KR | 10-1591379 | B1 | 2/2016 | |
| KR | 10-2016-0065562 | A | 6/2016 | |
| KR | 10-1779705 | B1 | 9/2017 | |
| KR | 10-2030272 | B1 | 10/2019 | |
| KR | 10-2019-0136580 | A | 12/2019 | |
| KR | 20190136580 | A * | 12/2019 | ........... G01N 27/308 |
| KR | 10-2021-0076854 | A | 6/2021 | |
| KR | 10-2021-0151487 | A | 12/2021 | |
| WO | WO 2019/208901 | A1 | 10/2019 | |
| WO | WO 2021/013392 | A1 | 1/2021 | |
| WO | WO 2021/224907 | A1 | 11/2021 | |

OTHER PUBLICATIONS

Tran et al., "Toward Intraoperative Detection of Disseminated Tumor Cells in Lymph Nodes with Silicon Nanowire Field Effect Transistors", ACS Nano, vol. 10, No. 2, published on Feb. 9, 2016, pp. 2357-2364.

* cited by examiner 203
202
205
2082
208
2061
206
209
2091
2081
281
2711
261
271
251
2552
2554
2551
255
2951
2553
2541
254
2111
241
211
2911
295
293
291
2912
292
294
296
2941
201
x
y
z

BIOSENSOR CARTRIDGE AND BIOSENSOR SYSTEM INCLUDING SAME

CROSS-REFERENCE TO RELATED APPLICATIONS

This application claims priority to the Korean Patent Application No. 10-2022-0047913 filed in the Republic of Korea on Apr. 19, 2022, which is hereby incorporated by reference into the present application.

BACKGROUND

Field

This disclosure relates to a biosensor cartridge having a biosensor and a biosensor system including the biosensor cartridge.

Discussion of the Related Art

Recently, as diseases having a high infectivity spread, a need for rapid diagnosis and self-diagnosis of the disease in medical fields such as homes, hospitals, and public health centers is increasing.

Therefore, it is required to develop an immunoassay platform that does not require specialized knowledge or complicated procedures and has a short analysis time.

A biosensor generates an electrical, optical signal, and a color that changes according to a selective reaction between probe material having reactivity for a specific target material contained in a body fluid such as sweat and saliva, or in biological substances such as blood or urine, and the target material. Accordingly, the presence of a specific target material can be checked by using the biosensor.

Conventionally, a strip-type rapid kit has been widely used, and simple color development (e.g., the test, such as a dipstick, will change colors if the results are positive) is performed by determining whether a bio-target material having a certain concentration or higher is present.

However, in the case of labeling the target material by color development, the conversion of color development can be inaccurate depending on the concentration of the target material, and the color development must be visually determined. Therefore, the accuracy is different depending on a user who views the test results.

To compensate for this inaccuracy, a biosensor that generates an electrical signal, as opposed to a color development, has been proposed.

In a biosensor that generates an electrical signal, a target material is coupled to a small thin film semiconductor structure, an electrical conductivity of the semiconductor structure is changed by the target material, and the target material is detected through a change in electrical conductivity. In particular, when a target material is combined (e.g., disposed) in a channel, if an electrochemical reaction occurs or the target material itself has a charge, electrons or holes in the semiconductor structure are accumulated or depleted due to the electric field effect caused by the combination of the probe material and the target material. Thus, the electrical conductivity is changed, which is read as a change in the amount of current. In such an electrochemical-based biosensor, the resistance of an electrode itself and the interfacial property of a channel where the electrochemical reaction occurs can be rather important.

Meanwhile, in the biosensor having a channel of semiconductor structure as mentioned above, an electrode for measuring an electrical signal is also manufactured in a dicing unit (e.g., a process where a sheet of electrodes is diced or cut into individual electrodes, which may be performed using a laser, for instance) and the thickness thereof is very thin, and damage of the electrode or channel can occur in a coupling process with a measurement device for measuring current, and therefore, a short circuit or contamination can occur.

To prevent this possibility of a short circuit, the conventional biosensor is provided as a structure including a sensor for sensing a target material and a connector for connecting with the measurement device.

That is, the electrode of the conventional biosensor is extended from the sensor for sensing a target material and includes the connector for connecting with the measurement device.

However, even in the case that the electrode is extendedly formed, since the electrode is formed in a dicing process, the size of the sensor chip becomes greater, which can cause a limitation that the semiconductor wafer becomes greater unnecessarily, and therefore, the chip yield can become degraded.

Furthermore, for the biosensor chip of which specimen is liquid and inducing reaction of the sensor chip, when the specimen flows into an area except a reaction area of the sensor chip, the specimen contacts other portion of the electrode, and there can be a limitation that a short current can occur.

For this, a structural modification is needed to accommodate the specimen, but it is hard to expect for a normal user to inject the specimen into an accommodation area accurately, and widening of the accommodation area for the specimen causes extension of the area of the entire cartridge, and accordingly, the cost can be increased, and the portability can be degraded.

SUMMARY OF THE DISCLOSURE

The disclosure has been made in view of the above limitations, and can provide a biosensor cartridge including a sensor chip, and provide an optimal structure of an accommodation portion to which specimen is injected in the cartridge.

The disclosure can further provide a biosensor cartridge capable of inducing valid reaction result even by a small amount of specimen by applying hyper water-repellent structure on a surface of a specimen accommodation portion of the cartridge.

The disclosure can further provide an optimal structure of an accommodation portion and a hyper water-repellent pattern by controlling an angle of the hyper water-repellent pattern of the accommodation portion.

In accordance with an aspect of the present disclosure, a biosensor cartridge includes: a circuit board including a connection terminal configured to be electrically connectable to an external diagnostic device; a sensor chip configured to detect a target material from an applied analysis specimen, have a reactant reacting specifically with the target material, and transmit an electrical signal generated by reacting with the detected target material to the connection terminal of the circuit board; and a housing configured to accommodate the circuit board and the sensor chip and surround the circuit board and the sensor chip so that the connection terminal is exposed, wherein the housing has an inclined surface dent from an upper surface and forms an accommodating portion that exposes the sensor area of the sensor chip and accommodates the test specimen, and wherein accommodating portion includes a pattern structure for lowering surface energy.

The accommodating portion of the housing can have an inclined area of which diameter is gradually decreased from an upper surface, and wherein an end of the accommodating portion can have an opening to expose the sensor area of the sensor chip therein.

A plurality of pattern grooves of a ring shape having different diameters with an opening at a center of the accommodating portion in a test area of the accommodating portion can be formed in an inclined area.

The plurality of the pattern grooves can have a first width and a predetermined separation distance, and can be disposed with being spaced apart from a neighboring pattern groove.

The first width can be 1.5 to 4.5 times of the predetermined separation distance.

The first width can be 100 to 250 μm, and the predetermined separation distance can be 80 to 160 μm.

A depth of the pattern groove can be 25 to 55 μm.

The pattern structure formed on the inclined area can have a micron size.

The pattern groove can include a bottom surface dent from the inclined area and a side surface extended from the bottom surface, and the side surface can be inclined with respect to the bottom surface by 90 degrees or greater.

The side surface of the pattern groove can be formed vertically with respect to the plane of the sensor area of the sensor chip.

The accommodating portion can further include a vertical area proximity to the sensor area in a lower portion of the inclined area, extended from the inclined area, and vertically formed.

The accommodating portion can further include a coating layer for lowering surface energy on a hyper water-repellent pattern structure.

The hyper water-repellent pattern structure can be formed by injection molding simultaneously with the housing.

The coating layer can be formed with fluorine-based polymer and includes one of PFA fluorine-based acrylate, methacrylate, or perfluoropolyether (PFPE).

The coating layer can be formed with a thickness smaller than a depth of the pattern groove.

The sensor area can include: a substrate, a channel area in which at least one of the channel is formed on the substrate, a source electrode and a drain electrode overlapped with both ends of the channel and formed spaced apart from each other, a gate electrode spaced apart from the source electrode and the drain electrode and introducing bias voltage to the analysis specimen, and a passivation layer for covering the entire sensor area and opening only an upper portion of the channel area and the gate electrode.

The housing can include an upper housing in which the accommodating portion is formed and a lower housing facing the upper housing, and the upper housing and the lower housing can be fused and integrated in a state of accommodating the sensor chip and the circuit substrate.

The accommodating portion can further include a guard protruded upwardly from the upper surface of the housing and accommodating the specimen.

The accommodating portion can further include a guide groove surrounding the guard on the upper surface of the housing and dent to accommodating the specimen flowing from the guard.

In accordance with another aspect of the present disclosure, a biosensor system includes: a biosensor cartridge including a connection terminal exposed at a side, the connection terminal outputting an electronic detection signal generated according to a target material from an applied analysis specimen; and a diagnostic device of an integrated shape, including an insertion hole to which the connection terminal of the biosensor cartridge is inserted, and for analyzing the detection signal from the biosensor cartridge from the insertion hole and reading a presence of the target material and displaying the reading on a display area, wherein the biosensor cartridge includes: a sensor chip including a sensor area reacting with the target material, a circuit substrate connected to the sensor chip and formed with the connection terminal at an end, and a housing for covering and accommodating the circuit substrate and the sensor chip and formed with an accommodating portion for accommodating the specimen by opening a part of the sensor chip thereon, and wherein the accommodating portion has a hyper water-repellent pattern structure to deliver the specimen to a part of the sensor chip which is open.

BRIEF DESCRIPTION OF THE DRAWINGS

The above and other objects, features and advantages of the present invention will be more apparent from the following detailed description in conjunction with the accompanying drawings, in which.

DETAILED DESCRIPTION OF THE EMBODIMENTS

Figure 1:
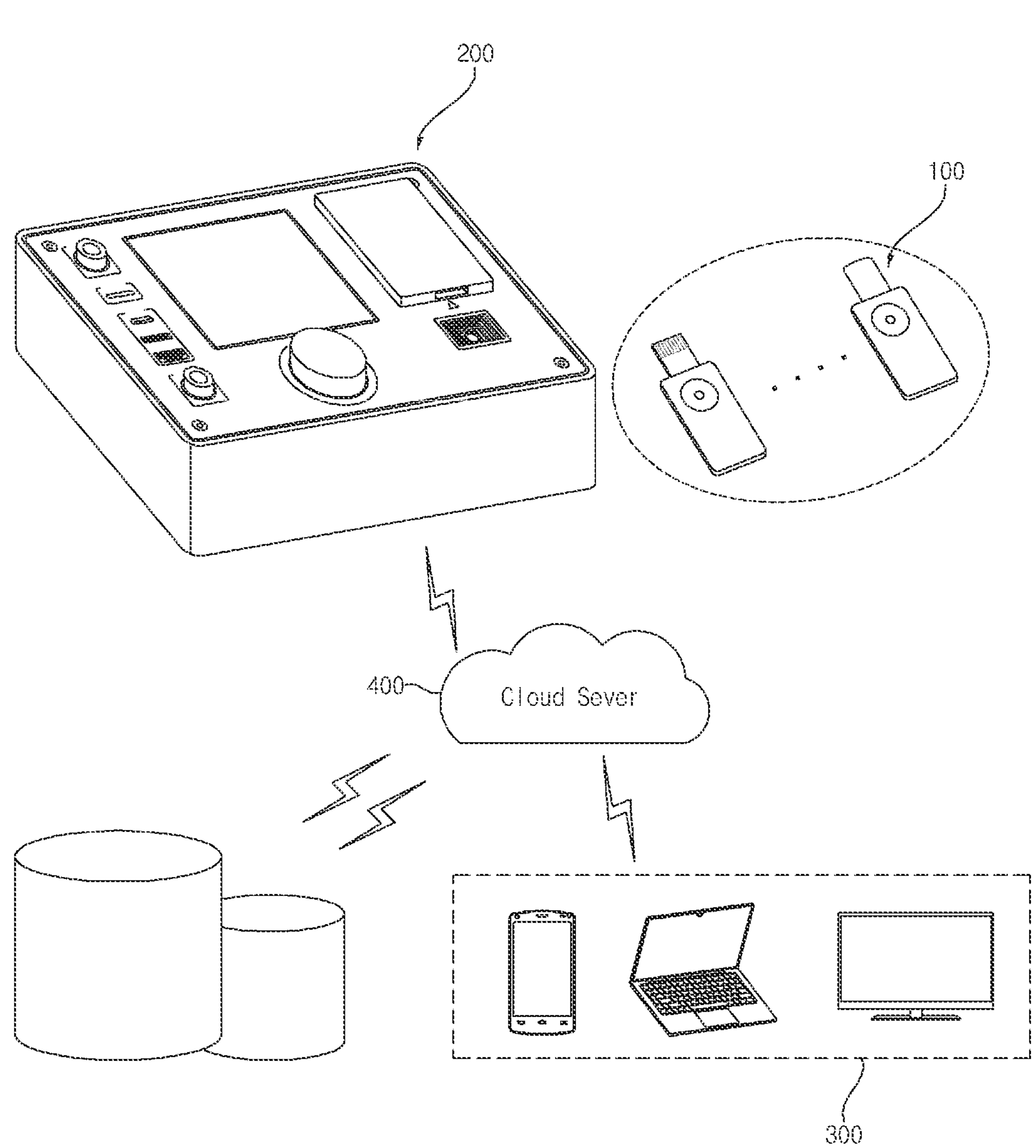
FIG. 1 is a diagram illustrating a biosensor system according to one or more embodiments of the disclosure.

Expressions referring to directions such as "front(F)/rear (R)/left (Le)/right (Ri)/up (U)/down (D)" mentioned below are defined as shown in the drawings, but, this is for the purpose of explaining an embodiment so that it can be clearly understood, and it is obvious that each direction can be defined differently depending on where standard is set.

The use of terms such as 'first, second', etc. added before the components mentioned below is only to avoid confusion of the referred components, and is irrelevant to the order, importance, or master-slave relationship between the components. For example, an embodiment including only a second component without a first component can also be implemented.

In the drawings, the thickness or size of each component is exaggerated, omitted, or schematically illustrated for convenience and clarity of description. In addition, the size and area of each component do not fully reflect the actual size or area.

In addition, angles and directions mentioned in the process of explaining a structure of the present embodiment are based on those described in the drawings. In the description of the structure in the specification, if a reference point for the angle and a positional relationship are not clearly mentioned, the related drawings can be referred to.

In the present specification, target materials are biomaterials representing a specific substrate, and are interpreted as having the same meaning as analytical bodies or analytes. In the present embodiment, the target material can be an antigen. In the present specification, probe material is a biomaterial that specifically binds to a target material, and is interpreted as having the same meaning as a receptor or an acceptor. In the present embodiment, the probe material can be an antibody.

The electrochemical-based biosensor combines the analytical ability of the electrochemical method with a specificity of biological recognition, and detects a biological recognition phenomenon for a target material as a change in current or potential, by immobilizing or containing a material having biological specificity, i.e., probe material such as an enzyme, an antigen, an antibody, or a biochemical material, on the surface of an electrode.

Hereinafter, a biosensor system according to the present embodiment will be described with reference to FIGS. 1 and 2.

Figure 2:
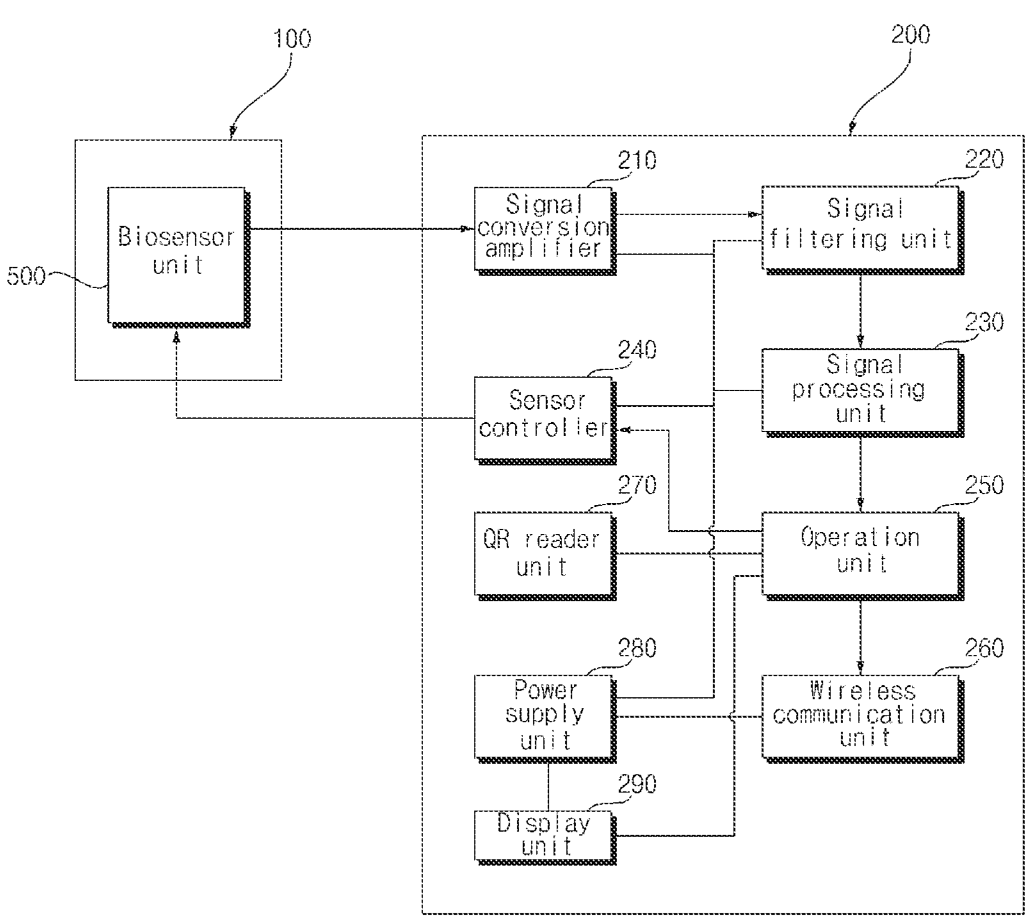
FIG. 2 is a configuration diagram of a biosensor diagnostic device and a biosensor cartridge of FIG. 1.

FIG. 1 is a diagram illustrating a biosensor system according to the present embodiment, and FIG. 2 is a configuration diagram of a biosensor diagnostic device 200 and a biosensor cartridge 100 of FIG. 1.

Hereinafter, a biosensor system according to the present embodiment will be described with reference to FIGS. 1 and 2.

FIG. 1 is a diagram illustrating a biosensor system according to the present embodiment, and FIG. 2 is a configuration diagram of a biosensor diagnostic device 200 and a biosensor cartridge 100 of FIG. 1.

Referring to FIG. 1, the biosensor system according to the present embodiment includes a biosensor diagnostic device 200, a plurality of biosensor cartridges 100, and at least one server 400.

When the plurality of biosensor cartridges 100 are inserted (e.g., the plurality of biosensor cartridges 100 can be inserted into the biosensor diagnostic device 200 simultaneously), the biosensor diagnostic device 200 reads a detection signal from the biosensor cartridge 100 to read the presence of a target material for each biosensor cartridge 100.

The biosensor diagnostic device 200 is a portable integrated diagnostic device 200 that detects a current change for the presence of a trace amount of a target material from the biosensor cartridge 100, and accordingly diagnoses a disease and delivers the diagnosis result to a user.

To this end, the biosensor diagnostic device 200 can be provided to be portable by integrating each functional block, miniaturizing it, and integrating it in one case.

The biosensor diagnostic device 200 can be moved regardless of location, regardless of the presence or absence of an external power source by mounting a battery 281 therein. In addition, the diagnostic device 200 includes a function of compensating a reproducibility and non-uniformity of a sensor by including a pre-processing process of correcting a detection signal from the biosensor cartridge 100 so as to be able to read a minute signal change.

In addition, the biosensor diagnostic device 200 includes a QR reader that reads a QR code disposed on the rear surface of the biosensor cartridge 100 and receives environmental information for genuine product certification of the biosensor cartridge 100 to perform genuine product certification and a communication module that can transmit and receive signals for genuine product certification with an external cloud server 400.

In the biosensor diagnostic device 200, a program algorithm or application for diagnosing a disease by measuring and analyzing the detection signal from the biosensor cartridge 100 can be installed, and different algorithms are executable according to the type of each biosensor cartridge 100. That is, each type of biosensor cartridge 100 will require a different algorithm or application, the different algorithms/applications are stored a memory of the biosensor diagnostic device 200.

In addition, the biosensor diagnostic device 200 includes a display unit 290 for directly displaying the diagnosis result to a user, and is designed to be directly manipulated through a user interface 296, 297, 294.

The detailed configuration of the integrated biosensor diagnostic device 200 will be described later.

Meanwhile, the biosensor system includes a plurality of biosensor cartridges 100 which is inserted into the biosensor diagnostic device 200 to provide detection signals.

Each of the biosensor cartridges 100 is electrically connected to a diagnostic device 200 in which an algorithm capable of measuring and analyzing an electrical detection signal generated in a biosensor chip 500 is installed.

Specifically, as shown in FIG. 1, the biosensor cartridge 100 can be inserted into and electrically connected to a cartridge insertion module 2911 of the integrated biosensor diagnostic device 200.

The biosensor cartridge 100 can accommodate the sensor chip 500 corresponding to a biosensor unit 500 (e.g., the sensor chip 500 can be designated a biosensor unit 500) in a housing 110, 120, and the housing 110, 120 can accommodate a circuit board 150 including a circuit pattern that extends to a connection terminal 153 that is connected to an electrode pad of the sensor chip 500 and inserted into the insertion module 2911 of an external biosensor diagnostic device 200.

The housing 110, 120 can be separated into an upper housing 110 and a lower housing 120, and the upper housing 110 and the lower housing 120 are coupled and fixed to each other while accommodating the sensor chip 500 and the circuit board, thereby constituting a single biosensor cartridge 100.

The biosensor cartridge 100 has a connection terminal 153 for physical and electrical coupling with the biosensor diagnostic device 200 exposed from one end to the outside, and a solution accommodating portion 119 for accommodating a specimen (e.g., analysis specimen) is formed on the surface (e.g., an upper surface) of the upper housing 110.

The solution accommodating portion 119 exposes a part of the inner sensor chip 500, and when a specimen is accommodated in the solution accommodating portion 119, the charge concentration of a channel of the sensor chip 500 is varied according to the antigen-antibody reaction of the sensor chip 500, so that the current flowing through the electrode of the sensor chip 500 varies. The varied current is read by the diagnostic device 200 through the connection terminal 153.

In this case, in order to secure the charge mobility of the sensor chip 500, a channel can be implemented with various materials, and in particular, a channel can be implemented by using graphene. However, alternate materials can be used for the channel of the sensor chip 500, such as silicon, silicon carbide, germanium, aluminum nitride, indium, gallium nitride and gallium arsenide.

The detailed configuration of the biosensor cartridge 100 will be described in detail later.

Meanwhile, the biosensor system can include at least one server 400.

The server 400 can be a manufacturer server 400, and the server 400 can include a processor capable of processing a program. The function of the server 400 can be performed by the manufacturer's central computer (e.g., a cloud computer).

For example, the server 400 can be a server 400 operated by a manufacturer of the biosensor cartridge 100 and the diagnostic device 200. As another example, the server 400 can be a server 400 that is provided in a building, and stores state information on devices in the building or stores content required by home appliances in the building.

The server 400 can store firmware information and diagnostic information on the diagnostic device 200, and transmit certification information on the biosensor cartridge 100 requested from the diagnostic device 200.

The server 400 in a biosensor system can be one of a plurality of cloud servers 400 of a manufacturer, and can be provided within the biosensor system while a plurality of cloud servers 400 are simultaneously included to allow access to one biosensor diagnostic device 200.

As described above, when a plurality of cloud servers 400 can simultaneously access one biosensor diagnostic device 200, the biosensor diagnostic device 200 can match the ranks with respect to the plurality of cloud servers 400, and can send a certification request sequentially from the highest priority. In this case, if a response signal is not received from the priority server 400, a certification request can be sent to the server 400 of the next priority.

The server 400 can authenticate the biosensor cartridge 100 and provide the certification result to the biosensor diagnostic device 200.

In addition, the server 400 can provide calibration data and update data for the product of a corresponding ID, and can transmit to the communicating biosensor diagnostic device 200.

The server 400 can also generate and distribute an upgraded version of a program for analysis for each biosensor cartridge 100.

To this end, the server 400 can receive history information on the manufacturing date, manufacturing conditions, sensor type, test result, etc. of the biosensor cartridge 100 of a manufacturer from a manufacturing server of a separate manufacturer.

In addition, the server 400 can periodically generate and distribute an upgraded version of a program provided to each diagnostic device 200 by receiving, accumulating, and machine learning the diagnostic result values for a corresponding product.

Meanwhile, the biosensor system of the present embodiment can further include a plurality of user terminals 300, but is not limited thereto. User terminals can include mobile terminals, laptops, touchpads, and the like.

When the user terminal 300 is included in the system, the biosensor diagnostic device 200 or the cloud server 400 can transmit data on the diagnosis result to the communicating user terminal 300.

To this end, a dedicated application for the user terminal 300 can be provided from the manufacturer server 400, and various processing of diagnostic data is possible by storing and executing the application in the user terminal 300.

For example, when a user is infected with the same disease for a long period of time, data processing is possible so that periodic test results can be accumulated and displayed, and the processed results can be provided to the user terminal 300 through an application. Accordingly, the user terminal 300 can be able to determine the prognosis for the disease and the expected treatment time.

The user terminal 300 can be, for example, a laptop, a smart phone, a tablet, or the like on which an application is installed.

The user terminal 300 can communicate (e.g., via wired or wireless communication) directly with the diagnostic device 200 or the server 400 through a network, and the diagnostic device 200 and the server 400 can also communicate directly through a network.

In this case, wireless communication technologies such as, IEEE 802.11 WLAN, IEEE 802.15 WPAN, UWB, Wi-Fi, Zigbee, Z-wave, and Blue-Tooth can be applied to the network, and can include a wireless communication unit 260 of each device (the user terminal 300 and the diagnostic device 200) to apply at least one or more communication technologies.

The wireless communication unit 260 can be changed depending on the communication method of other devices (the user terminal 300 and the diagnostic device 200) or the server 400 that is a target to communicate with.

As described above, in the biosensor system, the connection terminal 153 of the biosensor cartridge 100 accommodating the specimen is inserted into and electrically connected to the portable integrated biosensor diagnostic device 200 so that a detection signal is read.

The functional configuration of the biosensor diagnostic device 200 for reading the detection signal is shown in FIG. 2. Referring to FIG. 2, the biosensor diagnostic device 200 includes a plurality of function modules.

Each functional module can be individually packaged and accommodated in the case of one biosensor diagnostic device 200, and a plurality of functional modules can be packaged as one module and accommodated in a case 201, 202.

The biosensor diagnostic device 200 includes a signal conversion amplifier 210, a signal filtering unit 220, a signal processing unit 230, an operation unit 250, a wireless communication unit 260, a power supply unit 280, a display unit 290, a QR reader unit 270, and a sensor controller 240.

The signal conversion amplifier 210 receives firstly a detection signal transmitted from the biosensor cartridge 100, and converts and amplifies the current value of the detection signal so that the current value can be read by the biosensor diagnostic device 200.

The signal conversion amplifier 210 can have an analog circuit including a resistor that generates a voltage drop according to a changed current value which is a detection signal transmitted from the biosensor cartridge 100, and can further include an amplifying circuit that receives and amplifies such a voltage drop.

The amplified signal is transmitted to the signal filtering unit 220 to remove noise and then transmitted to the signal processing unit 230. The signal processing unit 230 can convert the amplified analog sensing value from which the noise has been removed into a digital value for a diagnostic operation, and can include an analog-digital converter (ADC) for this purpose.

As described above, the signal conversion amplifier 210, the signal filtering unit 220, and the signal processing unit 230 can all be implemented as a single integrated circuit chip. Such an integrated circuit chip can correspond to a cartridge insertion module 211 in FIG. 3.

The sensor controller 240 can provide a reference voltage whose level is changed according to the control of the operation unit 250 to the connection terminal 153 of the connected biosensor cartridge 100, and the biosensor cartridge 100 receives a reference voltage having a varied level from the sensor controller 240 and flows a current value changed by a varied resistance value of channel to the connection terminal 153. The connection terminal can be disposed at one side of the biosensor cartridge 100. The sensor controller 240 can be mounted together as a voltage level conversion circuit in the integrated circuit chip.

Meanwhile, the biosensor diagnostic device 200 includes an operation unit 250 for controlling the operation of the diagnostic device 200 and reading a received digitized detection value.

The control of the diagnostic device 200 can include a separate controller (e.g., hardware-embedded processor), but it is possible to simultaneously read whether a detection value is detected and control the operation of the entire diagnostic device by executing a program stored in one controller.

In this case, the operation unit 250 can be implemented as a separate integrated circuit chip, and can be mounted in a main board 255.

The operation unit 203 can read whether there exists a target material for the detection value according to the reading program, process the result and provide the result to the display unit 290. In addition, such a reading result can be transmitted to a cloud server 400 and a user terminal 300 through a wireless communication unit 260.

The operation unit 250 can also control the operation of the diagnostic device 200 for the reading. For example, when the connection terminal 153 of the biosensor cartridge 100 is inserted into the cartridge insertion module 211, the operation unit 250 can detect the insertion and transmit a QR reading command to the QR reader unit 270.

Accordingly, the QR reader unit 270 performs an operation for reading the QR code attached to the rear surface of the biosensor cartridge 100 inserted into the cartridge insertion module 211, and transmits the information back to the operation unit 250.

The operation unit 250 receives the QR information, performs a certification request to the cloud server 400 accordingly, and when certification information is received from the cloud server 400 and confirmed as genuine, performs reading for the biosensor cartridge 100, and matches the reading result with the certification result of the biosensor cartridge 100 and processes it.

Accordingly, the operation unit 250 can reduce an error by minimizing the time difference of the result matching (e.g., minimizing the time to determine if the biosensor cartridge 100 is genuine) by simultaneously executing the module control of the diagnostic device 200 and the execution of the read program.

The operation unit 250 can include a memory card (e.g., flash memory) as a data storage unit, a library file for diagnosing biomaterials, and an embedded system board equipped with a signal processing device. For example, a memory card capable of storing output signal data is inserted into the embedded system board, and a system operating system (OS), driving program, library file for analysis, and the like are stored in the memory card. In addition, signal processing for concentration analysis of biomaterials is calculated through comparison analysis with library files in the central processing unit (CPU) of the embedded system board, and the analyzed result is stored again in the memory card. In addition, the wireless communication unit 260 can be mounted together in such an embedded system board, but is not limited thereto.

The biosensor diagnostic device 200 includes a display unit 290 as a user interface, and the display unit 290 includes a liquid crystal display device, an OLED or LED display device, a touch panel, and the like to display an analyzed result detected by creating a program considering a user's convenience. As a user interface, it can include various types of terminals, dials, buttons, and the like.

A terminal 297, a dial 296, a button 294, and the like turn on/off the operation of the biosensor diagnostic device 200, and can be connected to the operation unit 250 to control the operation unit 250 according to a user command. That is, as a user's command is input in the interface 297, 296, 294, the diagnosis of the biosensor cartridge 100 can be started. The display unit 290 displays the progress process during the diagnosis process, and displays the diagnosis result after the completion of diagnosis.

The biosensor diagnostic device 200 includes a separate power supply unit 280 capable of applying power to a plurality of modules, and the power supply unit 280 includes a battery 281. Accordingly, it is possible to supply power to the internal module from the battery 281 and thus the device 200 can be portable. The battery 281 can be charged by an external power source, such as alternating current AC power available from the utility.

Hereinafter, a detailed structure according to an example of the biosensor diagnostic device 200 will be described with reference to FIGS. 3 and 4.

Figure 3:
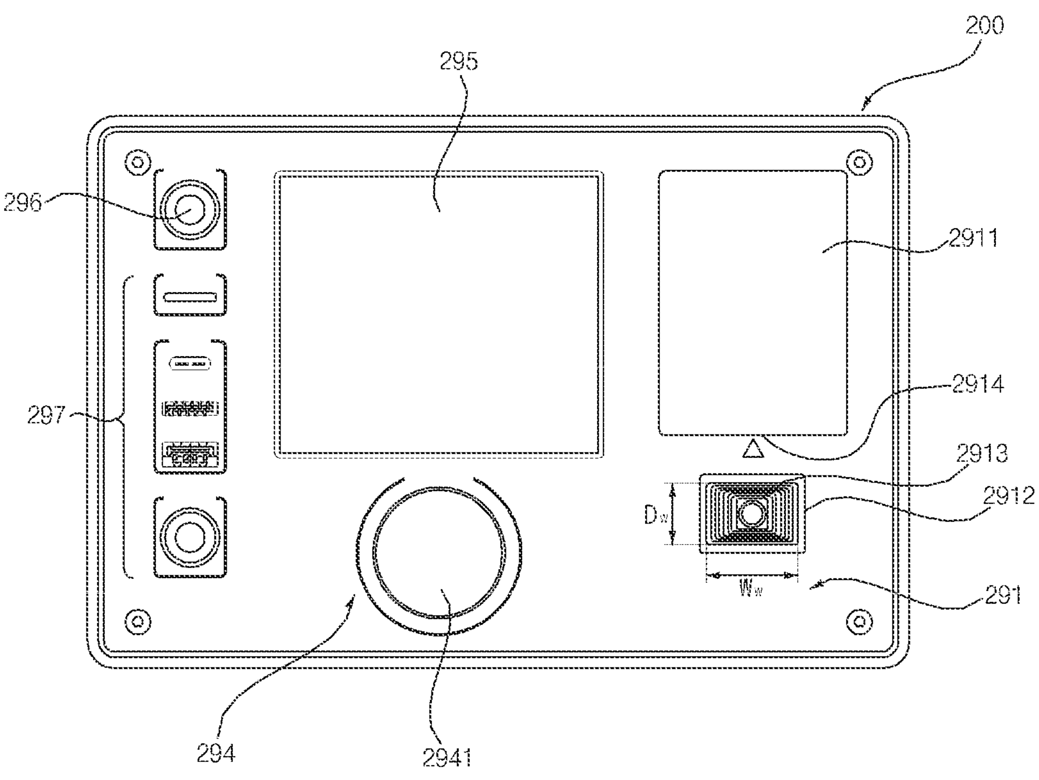
FIG. 3 is a front view of an example of the biosensor diagnostic device of FIG. 1.
Figure 4:
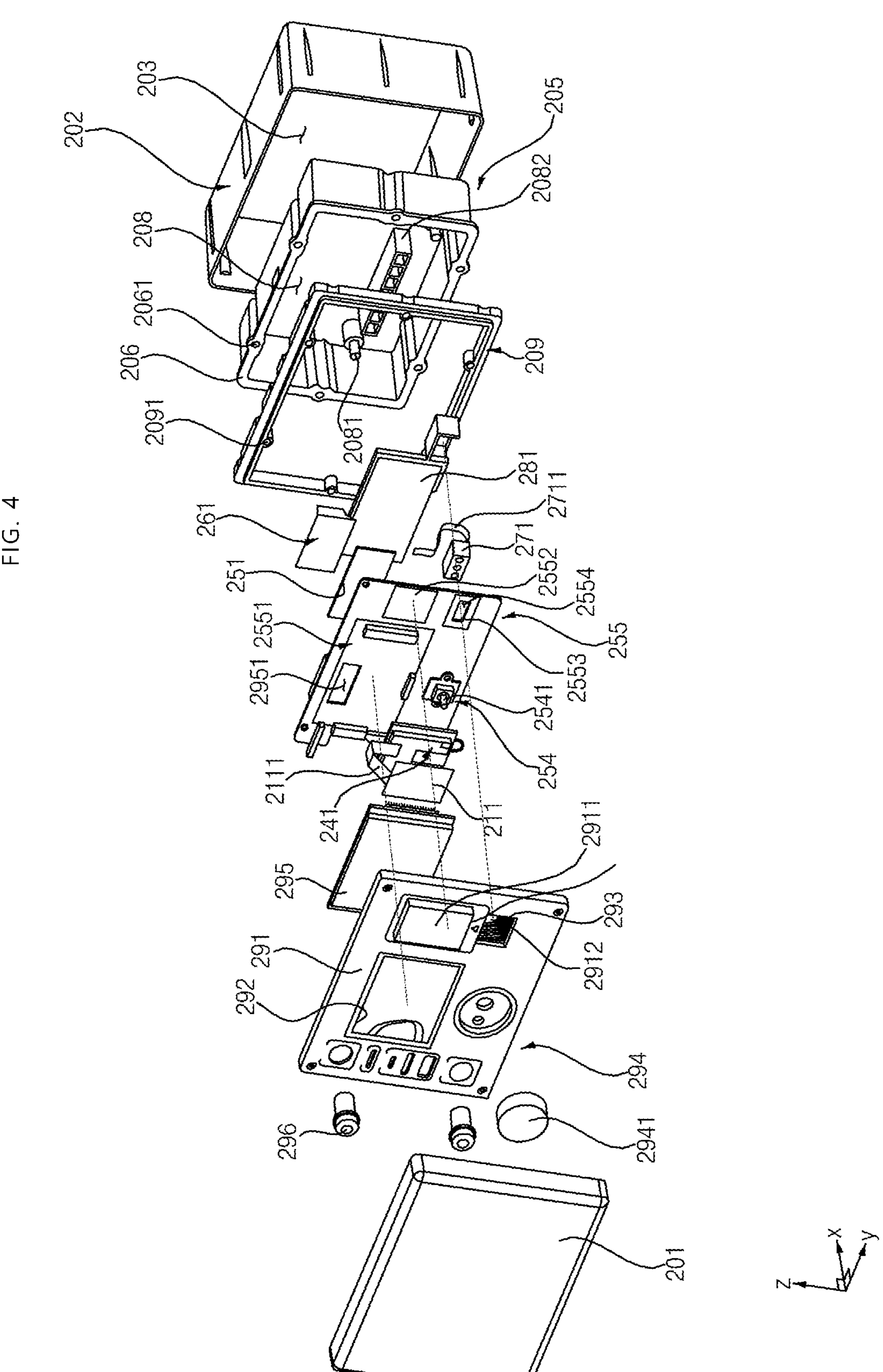
FIG. 4 is an exploded perspective view of the biosensor diagnostic device of FIG. 3.

FIG. 3 is a front view of an example of the biosensor diagnostic device 200 of FIG. 1, and FIG. 4 is an exploded perspective view of the biosensor diagnostic device 200 of FIG. 3.

Referring to FIGS. 3 and 4, the biosensor diagnostic device 200 according to the present embodiment is provided as a portable integrated device.

Here, the state of being integrated can include all states recognized as a single device in movement, disposition, and use of the diagnostic device 200. For example, the state of being integrated can mean that that it is located together inside the same case and is integrated by the same case, can mean that it is fixed by being fitted or attached to the same member and integrated by the same member, can mean that it is formed together in the same member to constitute a part of the same member, or can mean that it is wrapped or fixed together by the same member. On the other hand, it can be difficult to be considered as being integrated in the case of being connected by a separate output cable or the like.

The integrated biosensor diagnostic device 200 according to the present embodiment can include a separate inner cover 205 inside the case 201, 202. A front panel 291 is disposed to cover a plurality of modules accommodated in an accommodating portion 208 of the inner cover 205 and a front surface of the inner cover 205. In this case, one of a rear case 202 and the inner cover 205 can be omitted.

In the exploded perspective view of FIG. 4, the left side is defined as a front surface and the right side is defined as a rear surface along the X axis where the plurality of modules overlap, and the Y axis and Z axis perpendicular to the X axis are defined as two axes that forms a reference plane of the front panel 291 provided to a user.

The case 201, 202 of the biosensor diagnostic device 200 according to the present embodiment can include a front case 201 and a rear case 202. The rear case 202 is formed to have an accommodating portion 203 therein, and to have a bottom surface and a side surface. The accommodating portion 203 accommodates at least the inner cover 205, the main board 255 and the front panel 291. However, the accommodating portion 203 can accommodate all of the components of the diagnostic device 200 except for the front case 201.

The front case 201 and the rear case 202 can be disposed to face the accommodating portion 203 while the side surfaces are in contact with each other.

The accommodating portion 203 formed by the front case 201 and the rear case 202 is changed from an open space to a closed space according to the opening and closing of the front case 201.

An outer case accommodating the front case 201 and the rear case 202 simultaneously can be further formed. The outer case can be formed in a box type as shown in FIG. 3, can have a handle formed for easy portability, and have a pedestal formed to dispose the diagnostic device 200 at a certain angle.

The bottom surfaces of the front case 201 and the rear case 202 have the same size and define the total area of the biosensor diagnostic device 200.

The bottom surface can be formed in various shapes, and the shape can be a rectangle as shown in FIG. 4, but is not limited thereto, and can be a circle, an ellipse, a rhombus, or the like.

Meanwhile, when the shape of the bottom surface is a rectangle as shown in FIG. 4, the area is a portable size, and in the case of a polygon, one side can satisfy 30 cm or less, but it is not limited thereto, and it can be further miniaturized.

The height of the side surface forming the accommodating portion 203 of the rear case 202 can be greater than the height of the side surface of the front case 201, and the inner cover 205 is formed in the accommodating portion 203 of the rear case 202.

The inner cover 205 has the same shape as the rear case 202 so that it can be inserted into the accommodating portion 203 of the rear case 202, and the bottom surface of the inner cover 205 can have a smaller area than the rear case 202, but can be fitted to minimize a space between the side surface and the bottom surface of the rear case 202 and the side surface and the bottom surface of the inner cover 205. The inner cover 205 serves as a cover that achieves a substantial integration, and when the case 201, 202 is damaged, the inner cover 205 can be separated from the case 201, 202 and replaced. In addition, since the inner cover 205 is integrated with the rear case 202, one of the two can be omitted.

A plurality of modules are accommodated inside the accommodating portion 203 of the inner cover 205.

A supporter 2081, 2082 for supporting a module while defining the position of each module can be formed on the bottom surface of the inner cover 205, and the supporter 2081, 2082 can be variously designed depending on the disposition of the inner modules. The supporters 2081 and 2082 can be provided in plurality.

The main board 255 is accommodated in the accommodating portion 208 of the inner cover 205.

The main board 255 can be electrically connected to internal modules for executing a plurality of functions, and as shown in FIG. 4, a display module 295 constituting the display unit 290 and the cartridge insertion module 2911 in which the signal conversion amplifier 210 and the sensor controller 240 are integrated can be disposed in the front direction of the main board 255. In addition, a control switch 254 of the user interface of the front panel 291 can be disposed on the front surface.

An operation module 251 and a communication module 261 for controlling the operation of the control device and reading a detection signal according to a program can be disposed on the rear surface of the main board 255.

In addition, a QR reading module 271 can be disposed on the rear surface of the main board 255.

A battery 281 for applying power to the main board 255 and each of the functional modules is disposed, and the battery 281 can be disposed adjacent to the bottom surface of the inner cover 205.

Specifically, the front panel 291 includes a reference plane exposed on the front surface of the biosensor diagnostic device 200 as shown in FIG. 3.

The front panel 291 includes a first opening 292 for exposing a display module 295 that is disposed on the rear surface of the front panel 291 and displays an image on the front surface.

The first opening 292 can be covered with a transparent film, but is not limited thereto, and the display unit 290 of the display module 295 can be directly exposed.

A plurality of buttons, dials, and terminals 294, 296, 297 and the like for a user interface can be disposed around the first opening 291.

The plurality of buttons, dials, terminals 294, 296, 297, etc. can be adjusted in various forms according to design. For example, as shown in FIG. 3, a control dial 2941 can be disposed in a lower side of the first opening 292, and a plurality of terminals and dials 296 and 297 can be disposed also in the left side of the first opening 292, thereby receiving operation commands directly from a user. Meanwhile, the cartridge insertion module 2911 is disposed in the right side of the first opening 292 in the front panel 291, and in the right side of the reference plane. Alternatively, the cartridge insertion module 2911 can be disposed in the left side of the first opening 292 in the front panel 291, and in the left side of the reference plane.

The cartridge insertion module 2911 protrudes from the reference plane to the front surface, and includes a terminal portion to be electrically connected by inserting the connection terminal 153 of the cartridge in the Z-axis direction.

Accordingly, a terminal portion is formed in a side surface of the insertion module 2911, and the terminal portion can include at least one insertion hole 2914.

The insertion hole 2914 can be implemented in various ways depending on the shape of the connection terminal 153 of the cartridge. When the connection terminal 153 of the cartridge is formed in an SD card chip type, a USB type such as USB-A, USB-C type, or a PIN type, correspondingly, it can be formed to read an electrode of the connection terminal 153.

In addition, when the plurality of insertion holes 2914 are formed so as to read various types of connection terminal 153, the plurality of insertion holes 2914 can be disposed in parallel along the X-axis direction in the side surface of the insertion module 2911.

A second opening 293 for exposing the QR reading module 271 is disposed in the lower side of the insertion module 2911.

The second opening 293 is formed in a position aligned with the rear surface of the housing 101 of the cartridge 100 in the X-axis direction in a state in which the connection terminal 153 of the cartridge is inserted into the insertion hole 2914 of the cartridge insertion module 2911.

The second opening 293 can be covered with a transparent film, and the second opening 293 can have a rectangular shape, but an area of the second opening 293 can be smaller than that of the first opening 292. Further, the second opening 293 can have any shape corresponding to a shape of the QR reading module 271 or a QR area 2553.

The second opening 293 serves as a passage through which the QR reading module 271 disposed on the rear surface reads the QR code of the cartridge 100 that is placed on the front surface. In the second opening 293, a light guide part 2912 protruding from the rear surface of the front panel 291 to form a sidewall of the second opening 293 in order to maintain a distance between the QR reading module 271 and the cartridge 100 is formed.

The light guide part 2912 can serve as an illumination for photographing of the QR reading module 271 while maintaining the distance of the QR reading module 271. That is, the light guide part 2912 can include a light guide plate formed on a sidewall of the second opening 293.

A main board 255 in which each module is mounted is disposed on the rear surface of the front panel 291, and the main board 255 can also have a shape similar to the bottom surface of the inner cover 205.

The main board 255 is divided into a display area 2551 in which the display module 295 is disposed in correspondence with (e.g., overlapping in a front-rear direction) the area division of the front panel 291, a cartridge area 2552 corresponding to (e.g., overlapping in a front-rear direction) the cartridge insertion module 2911, a QR area 2553 corresponding to the second opening 293, and a control area 254 corresponding to the button and the dial for a user interface.

The main board 255 is a circuit board on which a circuit is patterned (e.g., layered or printed on) on the front and rear surfaces of the main body 255, and a connection terminal or a connector for electrical connection is disposed in each area. Each functional module can be integrated on the main board 255 after connecting the connection terminal of the board and connector and the connection terminal of each module or connector while being physically fixed in a defined area.

As shown in FIG. 4, a terminal module 241 in which the signal conversion amplifier 210, the signal filtering unit 220, and the sensor controller 240 are integrated is mounted in the cartridge area 2552 of the main board 255 corresponding to the cartridge insertion module 2911. The terminal module 241 can be connected to a insertion hole module 211 into which the connection terminal 153 of the cartridge is inserted by a flexible printed circuit board FPCB 2111, and unlike this, can be implemented as a single (e.g., unitary) component.

In addition, the display module 295 can be an LCD or LED panel module or any known type of display panel disposed in the display area 2551, and a terminal opening 2951 can be formed in the main board 255 in order to connect the operation module 251 on the rear surface of the main board 255 with the battery 281.

The operation unit 250 and the communication module 261 can also be connected to the main board 255 through a connector at the rear surface of the main board 255, but the disposition on the main board 255 is not limited thereto.

Meanwhile, the QR reading module 271 that reads a QR code through a QR opening 2554 formed in the QR area 2553 is disposed on the rear surface of the main board 255, and the QR reading module 271 is also electrically connected to the main board 255 through the flexible printed circuit board FPCB 2711 to receive power and control signals. That is, the QR reading module 271 can include the FPCB 2711 to electrically connect the QR reading module 271 to the main board 255.

A side frame 209 is formed for the disposition and fixing of such modules. The side frame 209 fixes the inner cover 205 and the front panel 291, and the inner cover 205 is fixed to the side frame 209 through a screw hole 2061 (or a plurality of screw holes 2061) extended from one end portion 206 of the side surface. Further, the side frame 209 is provided with multiple screw holes 2091 that overlap the screw holes 2061 of the inner cover 205. Fasteners, such as screws or bolts, pass through the screw home 2091 of the side frame 209, then are fixed to the screw holes 2061 of the inner cover 205. Each module is fixed at a specific position on the main board 255 through a plurality of other fixing parts, the main board 255 is physically fixed by coupling a screw and a screw hole between a plurality of fixing protrusions 2081 and 2082 protruding from the bottom surface of the inner cover 205 and the front panel 291.

Each module and component disposed therebetween is fixed by fixing the main board 255, the front panel 291, and the inner cover 205, and an electrical connection is maintained without being shaken during movement.

In addition, the front panel 291 and the inner cover 205 are fixed together through the screw hole and the screw of the side frame 209 to be integrated. Fixing and assembling of each component proceeds by the screw hole and the screw, thereby making it easy to disassemble and reassemble.

The front case 201, the rear case 202, the inner cover 205, and the front panel 291 can be formed of a resin such as polycarbonate or plastic for portability.

The biosensor diagnostic device 200 is, as shown in FIG. 3, provided to a user by exposing the front panel 291 in a form of having a space for accommodating a plurality of modules therein, and various external cases can be applied.

In particular, in the reference plane of the front panel 291 provided to a user as shown in FIG. 3, a screen of the display module 295 is provided, and various buttons and dials for a user interface are provided. In particular, a power button, a plurality of control buttons, and a USB terminal can be provided. In addition, the cartridge insertion module 2911 is provided to one side of the display module 295, and the connection terminal 153 is inserted into the insertion hole 2914 parallel to the reference plane of the panel 291, so that diagnosis of the biosensor cartridge 100 is possible.

Hereinafter, the biosensor cartridge 100 applied to the present embodiment will be described with reference to FIGS. 5 to 7.

Figure 5A:
FIGS. 5A and 5B are respectively top and rear views of an example of the biosensor cartridge of FIG. 1.
Figure 5A:
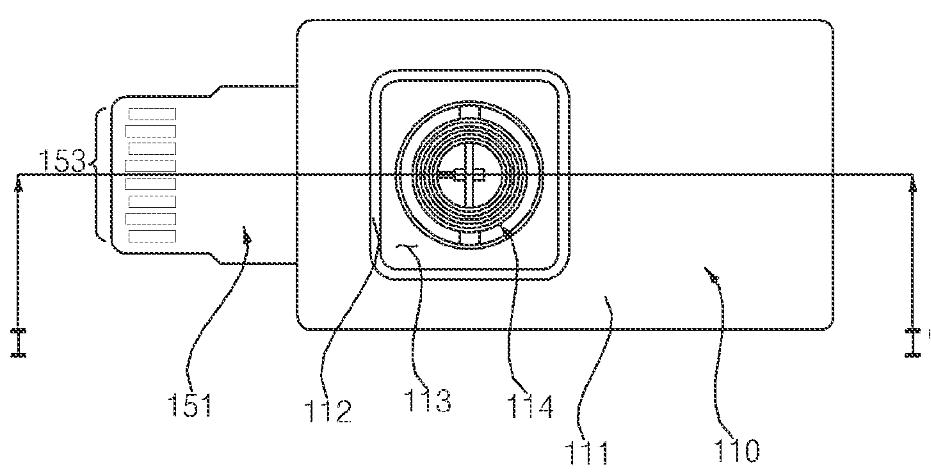
Figure 5B:
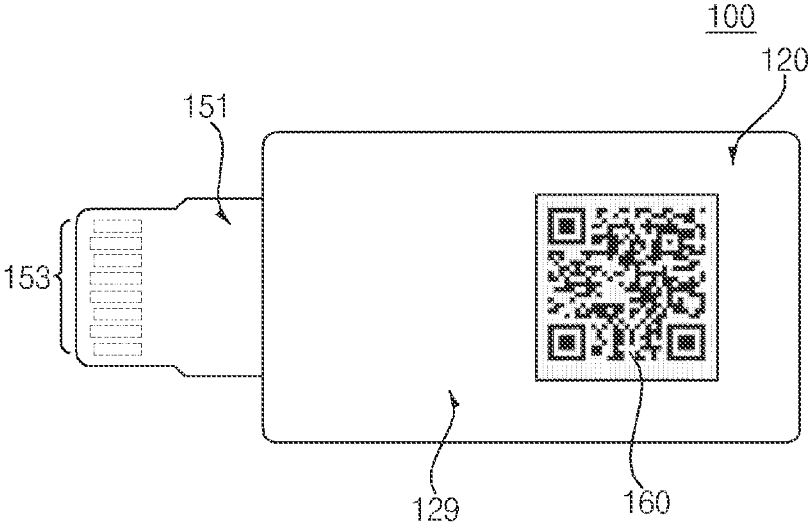
Figure 6:
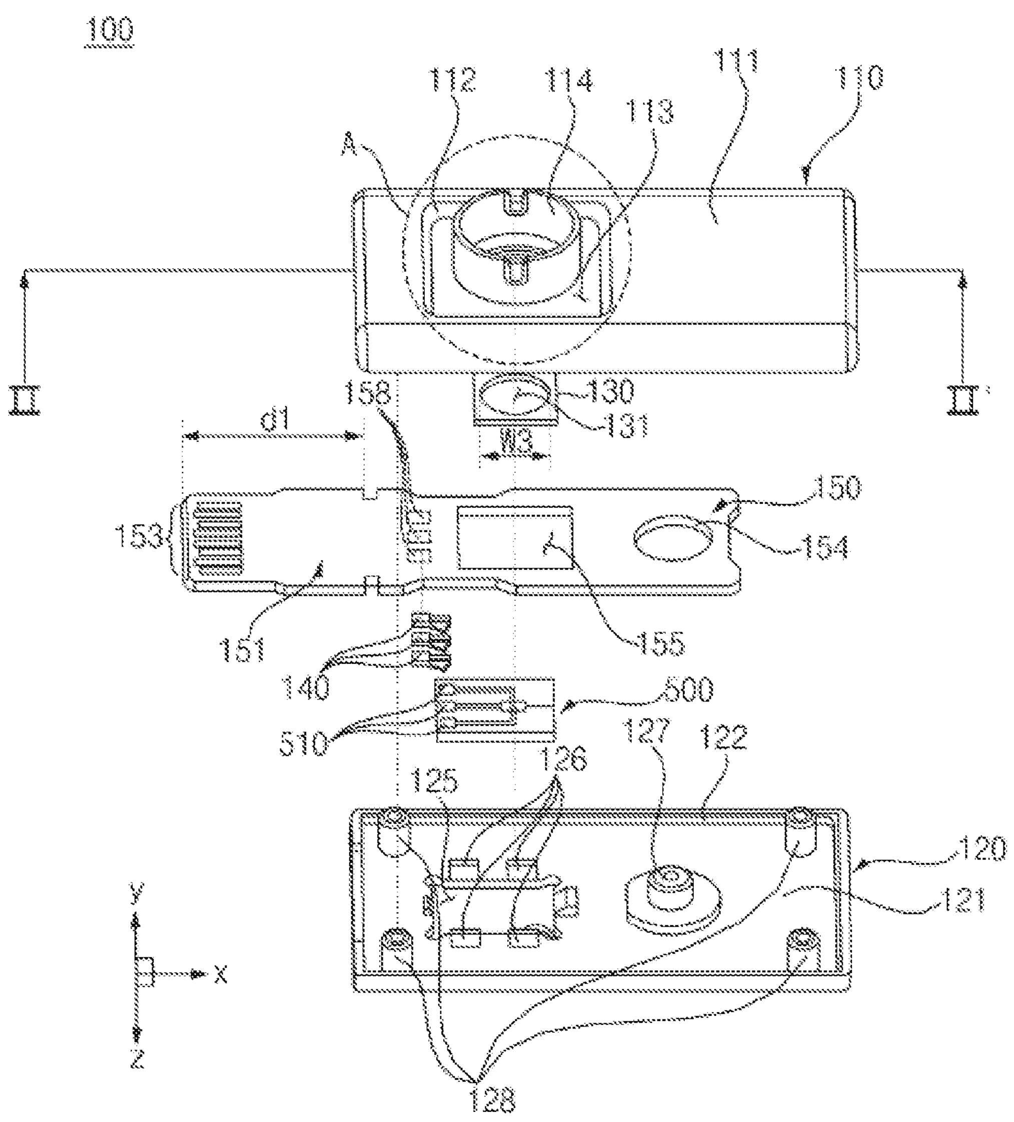
FIG. 6 is an exploded perspective view of an example of the biosensor cartridge of FIG. 1.
Figure 7:
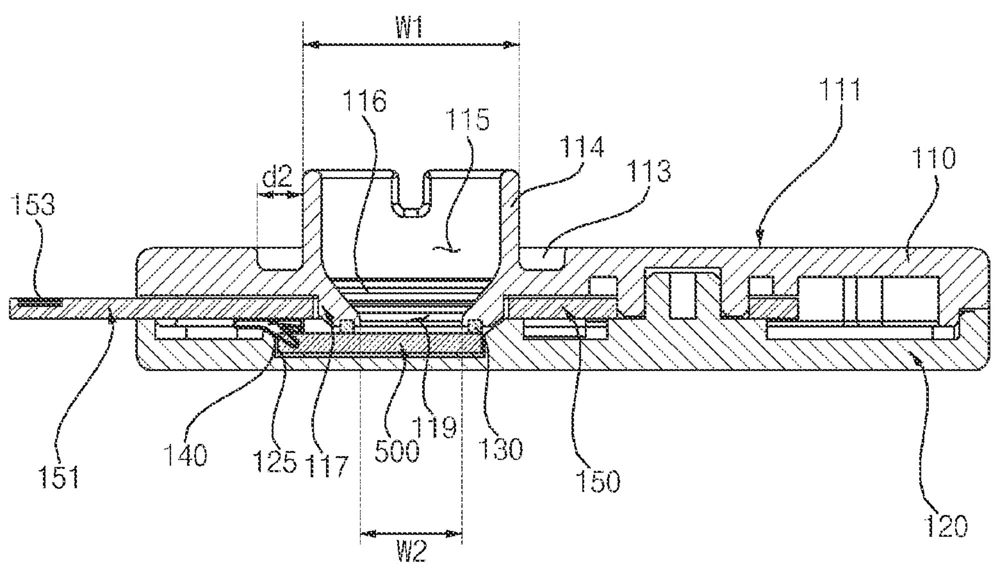
FIG. 7 is a cross-sectional view of the biosensor cartridge of FIGS. 5 and 6 taken along lines I-I' and II-II' of FIGS. 6 and 7, respectively.
Figure 8:
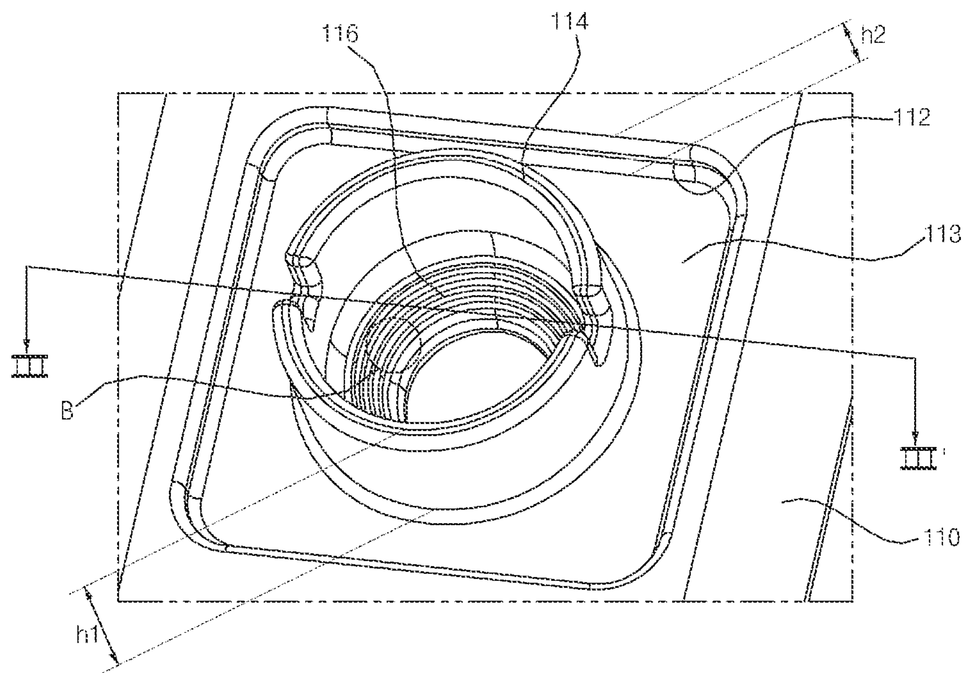
FIG. 8 is an enlarged view of "A" in FIG. 6.
Figure 9:
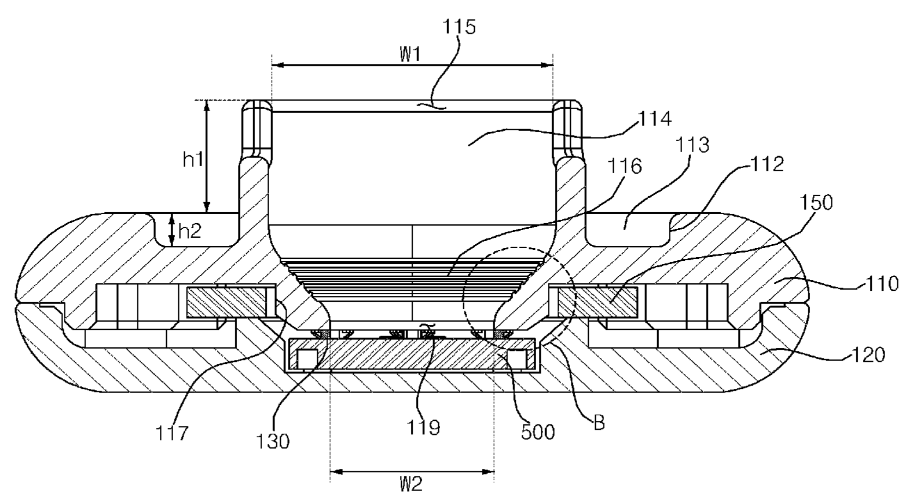
FIG. 9 is a cross-sectional view of the biosensor cartridge of FIG. 8 taken along lines III-III' of FIG. 8.
Figure 10:
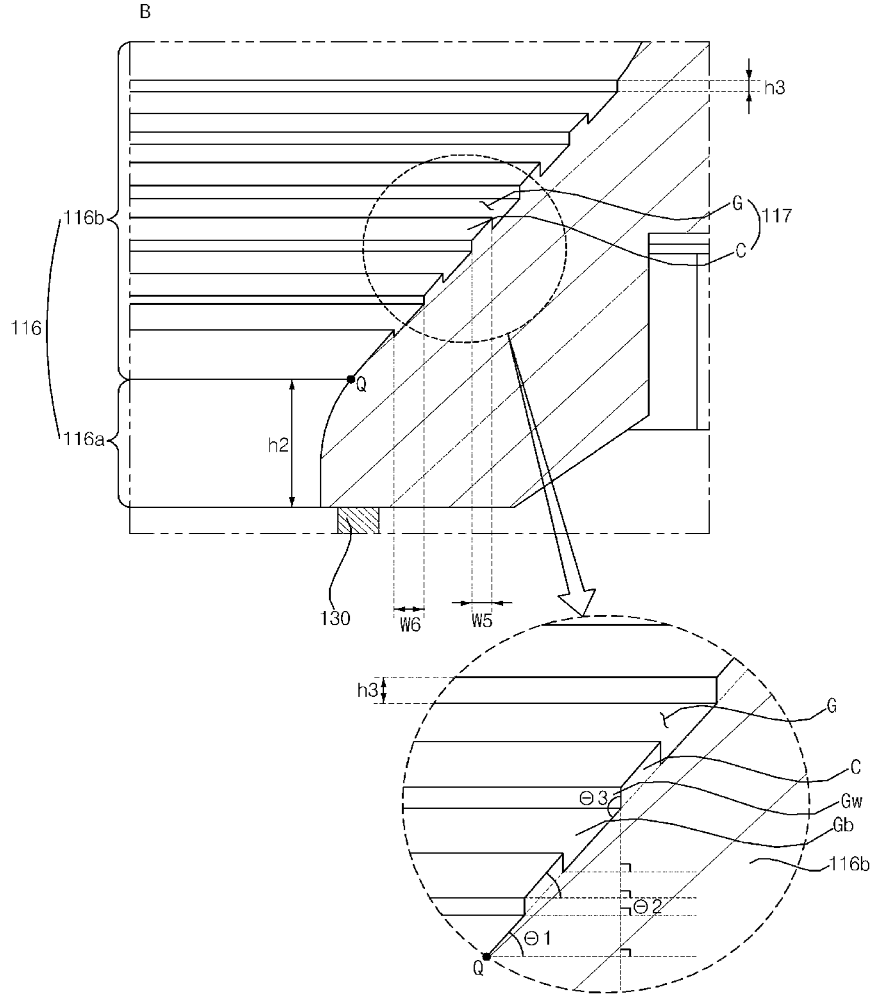
FIG. 10 is an enlarged view of "B" in FIG. 9.
Figure 11:
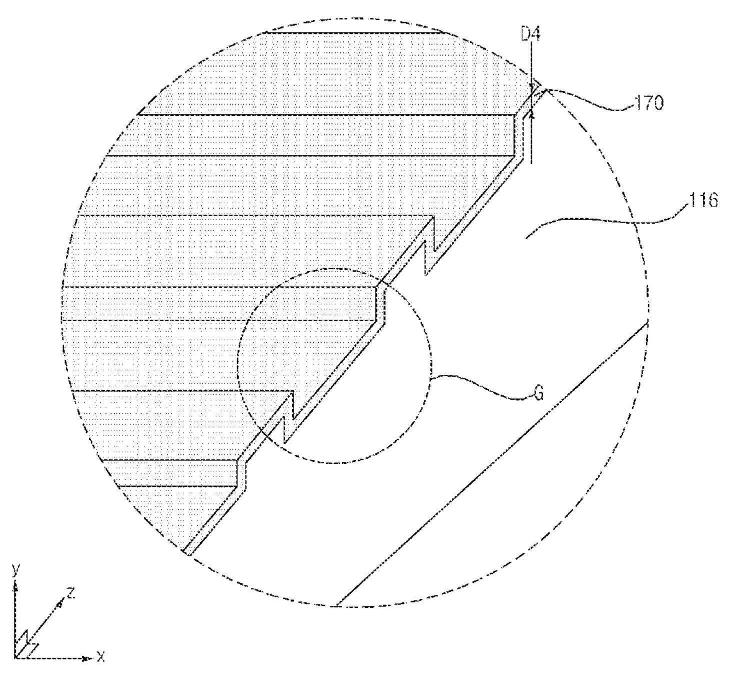
FIG. 11 illustrates another application example of the biosensor cartridge shown in FIG. 10.

FIGS. 5A and 5B are top and rear views of an example of the biosensor cartridge 100 of FIG. 1, FIG. 6 is an exploded perspective view of an example of the biosensor cartridge 100 of FIG. 1, and FIG. 7 is a cross-sectional view of the biosensor cartridge 100 of FIGS. 5 and 6 taken along lines I-I' and II-II'. In this case, FIG. 8 is an enlarged view of "A" in FIG. 6, FIG. 9 is a cross-sectional view of the biosensor cartridge of FIG. 8 taken along lines III-III' FIG. 10 is an enlarged view of "B" in FIG. 9, FIG. 11 illustrates another application example of the biosensor cartridge shown in FIG. 10, and FIG. 12A to FIG. 12C are views illustrating a contact angle of liquid according to a fine pattern.

FIGS. 5A to 12, the biosensor cartridge 100 according to the present embodiment accommodates a sensor chip 500 that generates an electrical detection signal according to a target material, and has a structure of including a connection terminal 153 capable of transmitting the detection signal to an external diagnostic device 200.

Specifically, the biosensor cartridge 100 is formed of a bar type housing 110, 120, a partial surface 151 of the circuit board 150 protrudes from the end surface of the side surfaces of the housing 110, 120, and a connection terminal 153 that is inserted into the external diagnostic device 200 and transmits the detection signal is formed on the partial surface 151 of the protruding circuit board 150.

The accommodating portion 119 for accommodating a specimen is formed on an upper surface 111 of the housing 110, 120, and a QR label 160 can be attached to the lower surface of the housing 110, 120.

The connection terminal 153, which protrudes from the side surface of the housing 110, 120 and is exposed, is disposed in the same direction as the lower surface of the housing 110, 120 and is not exposed when the cartridge 100 is viewed from the upper surface. Accordingly, it is possible to reduce the risk that the specimen flowing out of the accommodating portion 119 touches the connection terminal 153.

The biosensor cartridge 100 includes housing 110, 120, a sensor chip 500, and a circuit board 150.

The circuit board 150 is also formed in a bar type, and has one end where a connection terminal 153 is formed so that the connection terminal 153 of the circuit board 150 is coupled to be exposed to the outside of the housing 110, 120, thereby forming the entire shape of cartridge 100.

Specifically, the housing 110, 120 includes a lower housing 120 and an upper housing 110.

The lower housing 120 includes a bar-type bottom surface 121 (e.g., a planar shaped surface or a rectangular shape surface that is planar) and a side surface 122 surrounding the bottom surface 121. The bottom surface 121 includes a plurality of coupling protrusion 127, 128 protruding toward the upper housing 110, and the coupling protrusion 127, 128 is fitted with a coupling groove of the upper housing 110 so that the upper and lower portions of the housing 110, 120 are coupled and integrated. The lower housing 120 can include four coupling protrusions 128 positioned at corners of the lower housing 120, which are coupled to corresponding grooves of the upper housing 110 which are located at corners of the upper housing 110. The coupling protrusion 127 (e.g., substrate protrusion) can be from the other coupling protrusions 128 (e.g., corner coupling protrusions 128). Alternatively, more than four coupling protrusions 127 can be formed and the coupling protrusions can be equally spaced around a periphery of the lower housing 120.

A substrate protrusion 127 defining a position while fixing the circuit board 150 toward the upper housing 110 is formed on the bottom surface 121 of the lower housing 120, and a plurality of sensor protrusions 126 defining a chip area 125 in which the sensor chip 500 is disposed are formed in one side of the lower housing 120, the one side facing the upper housing 11.

The sensor protrusion 126 is disposed to correspond to the size of the sensor chip 500 so as to define a chip area 125 in which the sensor chip 500 is disposed, and is formed to have a certain elasticity (e.g., predetermined elasticity) so that the sensor chip 500 can be fitted. Each sensor protrusion 126 has a protruding structure having an inclination toward the chip area 125 so that it is not damaged by the edge of the sensor protrusion 126 when the sensor chip 500 is mounted. However, since the sensor protrusion 126 does not electrically connect the sensor chip 500, it can be implemented in various forms, and can be formed as a rail structure for sliding coupling in addition to fitting.

A sensor chip 500 is disposed in the chip area 125.

The sensor chip 500 is a semiconductor-based biosensor, and is divided into a sensor area 540 that reacts according to a target material in the specimen through contact with the specimen, and a pad area 510 for transmitting a detection signal generated according to the sensor area 540 to the circuit board 150.

The pad area 510 can be patterned to be disposed in one side of the sensor chip 500 as shown in FIG. 6, and accordingly, the electrical connection between the circuit board 150 and the sensor chip 500 is performed in the pad area 510.

The sensor chip 500 can have different sizes depending on the size of the cartridge, for example, can have a rectangular shape of 8 mm*6 mm, or can have a square shape of 6 mm*6 mm. The size of the sensor chip 500 can be variously implemented according to the performance of the sensor chip 500 or the purpose of the sensor chip 500.

The detailed structure of the sensor chip 500 will be described in detail later.

The circuit board 150 is disposed on the sensor chip 500.

The circuit board 150 can be provided as a rigid board like a printed circuit board (PCB), and the sensor chip 500 is electrically/physically bonded to the lower portion.

The circuit board 150 includes a sensor opening 155 through which a sensor area 540 of the sensor chip 500 is exposed, and the sensor opening 155 has a size smaller than that of the sensor chip 500. In addition, the opening 155 can have a size corresponding to the sensor area 540 of the sensor chip 500, and has a size to expose the sensor area 540.

The circuit board 150 further includes a protrusion hole 154 through which the substrate protrusion 127 of the lower housing 120 penetrates to fix the circuit board 150, and accordingly, the circuit board 150 and the lower housing 120 are fixed.

The circuit board 150 can be implemented by a plurality of circuit patterns patterned on a base member (not classified by reference numerals, denoted by 150 in the drawing) as the deposition structure thereof, and an insulating layer covering the circuit pattern.

The circuit pattern and the insulating layer can be formed on a rear surface of the base member, and a reinforcing plate (not shown) can be attached to the front surface of the base member. A rear surface of the circuit board 150 can be defined as a surface facing the lower housing 120, and a front surface of the circuit board 150 can be defined as a surface facing the upper housing 110.

The required strength at the time when a part of the circuit board 150 is used as the connection terminal 153 that is inserted into the diagnostic device 200 can be satisfied by attaching the reinforcing plate to the rear surface of the circuit board 150 as described above.

On the rear surface of the circuit board 150, a circuit pattern including a plurality of connection pads 158 for connecting to the sensor chip 500 is formed, and a circuit pattern that extends to the connection pad 158 to transmit the detection signal from the connection pad 158 to the external diagnostic device 200 is formed to be connected to the connection terminal 153 of the front surface.

Accordingly, the number of connection terminal 153 on the front surface of the circuit board 150 can be equal to or greater than the number of pads of the sensor chip 500.

The plurality of connection terminals 153 can be spaced apart from each other at one end of the exposed surface 151 of the circuit board 150, i.e., at one end of the circuit board 150 and disposed in parallel.

For example, when the sensor chip 500 has three pads, the number of the connection pads 158 of the circuit board 150 also satisfies three, and the number of the connection terminal 153 satisfies three or more.

The connection terminal 153 further includes terminals not electrically connected to each connection pad 158 and can be used as a terminal for electrostatic discharge (ESD) blocking.

As shown in FIG. 6, the circuit pattern patterned on the front surface of the circuit board 150 can include eight connection terminals 153. In such a connection terminal 153, when the sensor chip 500 is driven in multi-channel to be connected to a plurality of connection pads 511 and to transmit and receive signals, four connection terminals can be allocated as a connection terminal 153 for transmitting and receiving signals of each pad by connecting to the source pad, drain pad, and gate pad of the sensor chip 500 corresponding to each channel, and four connection terminals are applicable as a terminal for ESD and incoming detection signal generation.

Such a connection terminal 153 can be formed as an SD card pin type or a USB-A type depending on an embodiment, but a USB-C type having more terminals can also be utilized as shown in FIG. 1.

In addition, the connection terminal 153 can be implemented as a pin type, and more terminals can be implemented.

Thus, the number of pads of the connection terminal 153 can increase in proportion to the number of probe material applied to the sensor chip 500, i.e., the number of source electrodes (or the number of drain electrodes).

Meanwhile, the circuit board 150 includes a plurality of coupling grooves, and the plurality of coupling grooves are formed to be able to fit while specifying a position when the upper housing 110 and the lower housing 120 are coupled.

Meanwhile, the upper housing 110 has a structure where the upper surface 111 and the rear surface are different from each other as shown in FIG. 6.

The upper housing 110 faces the lower housing 120 and is coupled to the lower housing 120 and serves as an upper case capable of accommodating the circuit board 150 and the sensor chip 500 therein. In addition, an accommodating portion 119 exposing the sensor area 540 of the sensor chip 500 is formed in the upper housing 110 to accommodate a test target specimen.

The upper housing 110 is formed to have rigidity that can firmly support the connecting member 140 by pressing the connecting member 140 with a certain force. The connecting member 140 can be formed in plurality and can be conductive tabs (e.g., metal tabs) for connecting the connection pad 158 disposed on the circuit board 150 with the pads 511 of the sensor chip 500.

The upper housing 110 and the lower housing 120 can be configured to surround the surfaces of the sensor chip 500 and the circuit board 150 to protect the sensor chip 500 and the circuit board 150 from the outside. Due to the strong coupling between the upper housing 110 and the lower housing 120, the specimen provided to the sensor chip 500 through the accommodating portion 119 can be prevented from leaking into the housing 110, 120.

At this time, when the upper housing 110 and the lower housing 120 are coupled, an opening through which the connection terminal 153 of the circuit board 150 protrudes is formed in one side (e.g., a first side) of the side surface, e.g., in a cross-section, so that the connection terminal 153 is exposed to a cross-section, and is inserted into the insertion hole 2914 of the external diagnostic device 200 as the connection terminal 153 of the cartridge.

The accommodating portion 119 for exposing the sensor area 540 of the sensor chip 500 and accommodating a specimen is formed on the upper surface 111 of the upper housing 110. The accommodating portion 119 is a space for inducing a reaction with the exposed sensor area 540 by accommodating a test target specimen in a fluid state, e.g., in a liquid state, and the accommodating portion 119 forms a conical channel whose diameter becomes narrower as it approaches the sensor area 540 from the upper surface 111.

Hereinafter, referring to FIG. 8 to FIG. 12, the accommodating portion 119 of the upper housing 110 is described in detail.

The accommodating portion 119 is formed to have an inclined surface 116 such that a diameter W1 of the opening of the upper surface is larger than a diameter W2 of the opening at the distal end of the accommodating portion 119.

The diameter w2 of the opening at the distal end of the accommodating portion 119 can be 3 mm to 6 mm. Preferably, it can satisfy 3.8 to 4.5 mm, more preferably 4 mm to 4.3 mm. However, it is not limited thereto and can be variable depending on the overall size of the cartridge 100 and the size of the sensor chip 500.

At this time, a first inclination angle θ1 of the inclined surface 116—the angle of the inclined surface 116 with respect to the horizontal direction (x-axis) in which the sensor chip 500 is placed, when viewed from the cross section in FIG. 7—can be uniform, but of the inclined surface 116 can have an inflection point (Q).

That is, the first inclination angle θ1 increases as it approaches the sensor area 540, and it forms a verticality in the outermost area 116*a* closest to the sensor area 540, so that it can be changed to a cylindrical passageway.

In other words, as shown in FIG. 10, the inclined surface 116 has the inclined area 116*b* having the first inclination angle θ1, and the lower portion of the inclined area 116*b* passing the inflection point (Q) is extended from the inclined area 116*b* and has the outermost area 116*a* which is vertical to the horizontal direction (x-axis).

As described above, since the accommodating portion 119 has the inclined surface 116, a concave groove having a depth that is a height from the upper surface of the upper housing 110 to the sensor area 540 is formed. A specimen is collected in the groove to induce a reaction with the probe material in the sensor area 540.

Meanwhile, the accommodating portion 119 further includes a guard 114 for preventing the specimen of the accommodating portion 119 from flowing to the outside as shown in FIGS. 5A to 9. The guard 114 can be formed in a cylindrical shape, and is formed to surround the opening of the upper surface 111 of the upper housing 110 and protrude upward (in the y-axis) from the upper surface 111.

Accordingly, the diameter W1 of the guard 114 can be the same as the diameter of the opening of the upper surface 111.

A guard groove 113 of a certain depth is formed on the upper surface 111 of the upper housing 110 while surrounding the accommodating portion 119. The guard groove 113 is to prevent the specimen overflowing from the accommodating portion 119 from flowing out of the housing 110, and is formed to be recessed by a certain depth h2 from the upper surface 111.

The depth of the guard groove 113 can be formed to satisfy ⅓ to ½ of the thickness of the upper surface of the upper housing 110.

The guard groove 113 can be formed in a circular shape identical to the shape of the guard 114, but can be formed in a rectangular shape having a minimum distance d2 or more from the guard 114 as shown in FIG. 6.

The height of the guard 114 can be greater than the depth of the guard groove 113, and can have a height equal to or smaller than the overall thickness of the housing 110, 120.

As described above, the accommodating portion 119, where the specimen and the sensor area 540 contact each other, firstly has a concave cup shape to accommodate the specimen and provides a space where the target material of the specimen and the probe material of the sensor area 540 react with each other. In addition, the accommodating portion 119 forms a guard 114 surrounding the opening of the upper surface 111 to secure the amount of the specimen by accommodating the overflowing specimen secondarily, and to prevent the risk of exposing the specimen to the outside.

In addition, tertiarily, the guard groove 113 is formed around the guard 114 to accommodate the specimen when the specimen overflows the guard 114 or flows to the outside of the guard 114, thereby preventing the specimen that can contain hazardous substances from exposing to the outside.

Thus, the test can be safely performed by changing the shape of the accommodating portion 119 for accommodating the specimen in the upper housing 110.

As described above, the accommodating portion 119 of the upper housing 110 accommodates the liquid specimen, and the specimen is randomly injected into the accommodating portion 119, and it is hard to adjust an amount of the specimen.

That is, in the case that a large amount of the specimen is injected into the accommodating portion 119 for prompt and accurate reaction, depending on the restriction of a size of the biosensor cartridge 100 and an accommodation volume of the accommodating portion 119, there is a danger that the specimen flows into an area deviating the guard 114 of the accommodating portion 119.

As such, the specimen flows outside, since the specimen can have dangerous pathogen and fatal to a user, and since the specimen flowing outside is in a liquid state, the specimen injected into the diagnostic device 200 and contacting the connection terminal 153 can cause a damage of the electronic device.

Therefore, according to the present embodiment, a hyper water-repellent pattern structure 171 is applied to the accommodating portion 119 such that the entire specimen is captured in the sensor area 540 of the sensor chip 500 exposed by the lower opening of the accommodating portion 119, and sufficient reaction can be induced, even in the case that a small amount of the specimen is injected.

Particularly, referring to FIG. 10 and FIG. 11, when the inclined surface 116 of the accommodating portion 119 has the inclined area 116*b* inclined with the first inclination angle 61, a plurality of the hyper water-repellent pattern structure 171 is formed in the inclined area 116*b*.

The hyper water-repellent pattern structure 171 is a structure to lower the surface energy of the inclined area 116*b*.

As the surface energy of the inclined area 116*b* is lower, the water contact angle becomes greater on the surface, and an amount of the captured specimen becomes smaller.

In the case that a small amount of specimen is injected into the inclined surface 116, owing to the low surface energy of the inclined surface 116, the specimen is not fixed on the inclined surface 116 but induced to flow downwardly.

The hyper water-repellent pattern structure 171 includes a plurality of pattern grooves G that forms a concentric circle centering around the lower opening of the accommodating portion 119 and a protrusion C between the pattern groove G as shown in FIG. 10, and the pattern groove G and the protrusion C are alternatively formed and form the hyper water-repellent pattern structure 171.

That is, when a bottom surface Gb of the pattern groove G and a side surface Gw of both sides of the bottom surface Gb form the pattern groove G, the side surface Gw of the pattern groove G forms the side surface Gw of the protrusion C.

The continual pattern structure 171 can be entirely formed throughout the inclined surface 116 of the inclined area 116*b*.

Each pattern groove G has a ring shape, and a plurality of pattern grooves G has the same center of the ring shape and is formed along the circumference of circles having different diameters, and accordingly, not overlapped with each other.

The contact angle θa of the pattern groove G with the liquid specimen can be changed depending on a width W6 of the pattern groove G, a distance between the pattern grooves G, that is, a width of the pattern protrusion C.

Figure 12A:
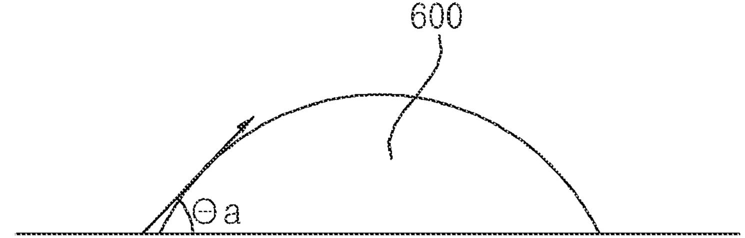
FIG. 12A to FIG. 12C are views illustrating a contact angle of liquid according to a fine pattern.
Figure 12B:
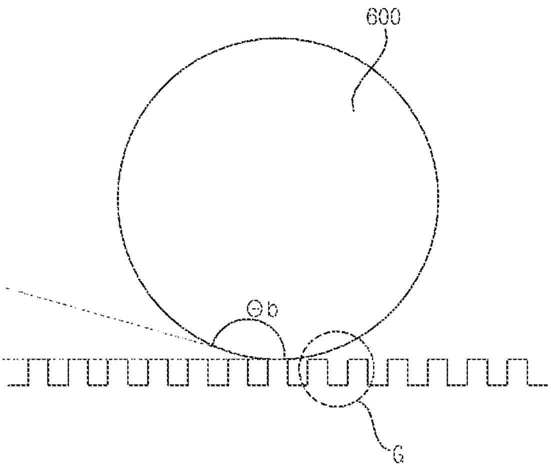

As shown in FIG. 12A, as the surface energy of the surface is higher, the liquid flowing on the surface is attached on the surface and stops, and unable to maintain a sphere shape of the liquid trajectory. Such a state is defined as a Wenzel state, hydrophilic or wetting of the surface state. On the other hand, as shown in FIG. 12B, in the case the liquid trajectory maintains a sphere shape and the contact angle θb of the surface of the liquid is 100 degrees or greater, the state is defined as a Cassier-Baxter state, that is, a hydrophobic or water repellent state.

Therefore, when the surface energy is very low, and the surface has the water repellent property, the contact angle between the liquid trajectory of the liquid that flows on the surface and the surface satisfies 100 degrees or greater, and the liquid flows on the surface without wetting. In addition, when the contact angle is 120 degrees or greater, the liquid has hyper water-repellent property.

On the inclined area 116*b* of the accommodating portion 119 according to the embodiment, the pattern structure 171 to have the hyper water-repellent property is formed, and the structure 171 to maintain the hyper water-repellent property can be maintained by controlling the width W6 of the pattern groove G and a separation distance W5 between the pattern grooves G, that is, a width of the pattern protrusion C.

Particularly, when a depth h3 of the pattern groove G is fixed to 25 μm to 55 μm, preferably, 30 μm to 50 μm, the pattern structure 171 for hyper water-repellent property can be implemented to control the width W6 of the pattern groove G and the separation distance W5.

The depth h3 of the pattern groove G satisfies the numerical range by considering the accommodation volume of the accommodating portion 119.

The width W6 of the pattern groove G can be 1.5 to 4.5 times of the width W5 of the pattern protrusion C.

In this case, preferably, the width W6 of the pattern groove G satisfies 100 to 250 μm, and the width W5 of the pattern protrusion C, that is, the separation distance W5 between the pattern grooves G can satisfies 80 to 160 μm.

As described above, the pattern of micron unit is formed, and sufficient hyper water-repellent property can be implemented. A pattern of a size greater than a nano pattern can be formed and formed together with the injection molding process of the upper housing 110, not formed by a laser process.

Accordingly, the manufacturing cost can be saved, a damage of the pattern by the laser process can be decreased, a sufficient separation distance between the pattern protrusions C is secured, and quality failure can be decreased.

As described above, a plurality of pattern grooves G of a ring shape formed in the inclined area 116*b* is continually formed and has the hyper water-repellent property, and the specimen contacting the inclined area 116*b* is flowed into the sensor area 540.

In this case, the bottom surface Gb of the pattern groove G of the pattern structure 171 having the hyper water-repellent property is inclined with the first inclination angle θ1, which is the same as the inclination angle of the inclined surface 116, and the inclination angle of the bottom surface Gb of the pattern groove G can be the same.

Furthermore, the side surface Gw of the pattern groove G can be formed vertically (θ2) with respect to a horizontal surface, that is, the surface (X axis) on which the sensor chip 500 is placed. Therefore, the angle θ3 between the pattern groove G and the bottom surface Gb has 90+the first inclination angle.

As such, the side surface Gw of the pattern groove G is inclined to the bottom surface Gb with the angle θ3, which is greater than 90 degrees, in the injection molding process for forming the pattern, a separation angle from the mold is not separately controlled, and the pattern is separable along a vertical direction.

In addition, in the vertical pattern structure 171 with respect to the horizontal surface, the specimen is vertically fallen and accommodated in the same way, the collision energy in falling.

At this time, the upper surface of the pattern protrusion C can be inclined with the same angle as the bottom surface Gb of the pattern groove G.

Meanwhile, as shown in FIG. 11, a hyper water-repellent coating surface 170 can further be formed on the inclined surface 116.

The hyper water-repellent coating surface 170 can be formed only on the inclined surface 116, but alternatively, formed on the entire accommodating portion 119, that is, the whole of the inclined surface 116, the protrusion C and the protrusion groove G.

The hyper water-repellent coating surface 170 can be formed by conformal coating with fluorine-based substance in a uniform thickness. The fluorine-based substance can include PFA fluorine-based acrylate, which is fluorine-based polymer H2C═CHCO2(CH2)xCyFz, methacrylate, or PFPE (perfluoropolyether).

The hyper water-repellent coating surface 170 can be formed to have a fourth thickness d4, and the thickness can be dozens of nm or a few μm.

That is, the thickness of the hyper water-repellent coating surface 170 is formed substantially lower than the height of the protrusion, and does not offset the hyper water-repellent pattern structure 171.

Figure 12C:
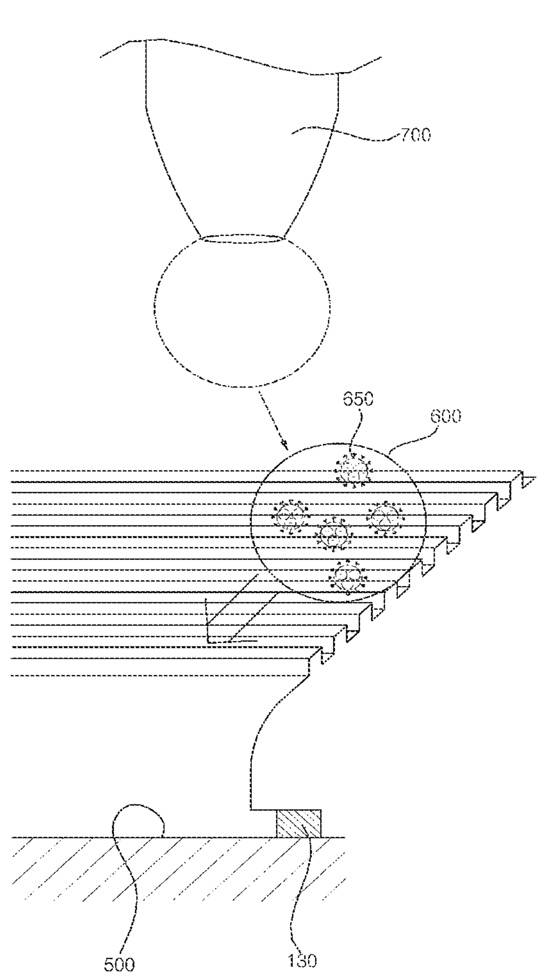

As shown in FIG. 12C, according to the biosensor cartridge of the present embodiment, the hyper water-repellent pattern structure 171 is formed on the inclined surface 116 of the accommodating portion 119, and in the case that the specimen 600 falls on the inclined surface 116 having the first inclination angle θ1 from an exterior 700, even a part of the specimen 600 falls on the inclined surface 116, the specimen 600 is not absorbed on the inclined surface 116 due to the low surface energy of the inclined surface 116 and flows downwardly with a high contact angle.

That is, owing to the pattern structure 171 that lowers the surface energy together with the structure of flowing downwardly by the first inclination angle θ1 of the inclined surface 116, the specimen 600 flows downwardly directly without being absorbed on the inclined surface 116, and accordingly, the entire specimen 600 is captured in a center area quickly.

Therefore, even in the case that a small amount of specimen 600 is injected, the entire specimen 600 is captured in a center area located in the lower part without being absorbed by other structure, and the amount of injection of the specimen 600 can be decreased, and since the amount of the specimen 600 is decreased, the danger that the specimen 600 flows outside can be significantly decreased.

Meanwhile, the rear surface of the upper housing 110 can include the inclined portion such that the inclined surface 116 of the accommodation portion 119 is formed.

Accordingly, as shown in FIG. 9, the sensor area 540 of the sensor chip 500 is exposed upward by the sensor opening 115 of the circuit board 150, and the lower opening of the accommodating portion 119 aligns with the exposed sensor area 540. The area of the accommodating portion 119 closest to the sensor area 540 is called the distal end, and the area furthest from the sensor area 540, which is opposite to the distal end, is considered the opening or outermost area. The distal end has a diameter W2 that is smaller than the diameter W1 of the opening/outermost area.

At this time, the opening 115 of the circuit board 150 is fitted to surround the rear surface of the inclined surface 116 of the accommodating portion 119, thereby fixing the positions of the circuit board 150 and the upper housing 110.

In addition, to this end, the rear surface of the inclined surface 116 of the accommodating portion 119 is formed to have a vertical step 117 in an area where it meets the opening 115 of the circuit board 150.

That is, the rear surface of the inclined surface 116 of the accommodating portion 119 forms an inclined portion along the inclined surface 116 at an angle equal to or greater than the inclination angle of the inclined surface 116 of the accommodating portion 119, and is inclined at an angle equal to or greater than the inclined surface 116 to form a space coupled to the circuit board 150.

At this time, at a portion to which the opening 155 of the circuit board 150 is coupled, a step 117 corresponding to the cut surface of the opening 155 of the circuit board 150 can be formed for fitting with the opening 155 of the circuit board 150. Accordingly, the step 117 can be formed perpendicular to a horizontal plane (x-axis on which the sensor chip is placed).

The step 117 can have a spaced distance from the side surface of the opening 155 of the circuit board 150, but is not limited thereto, and can be fitted and coupled.

It is easy to fix the circuit board 150 in case of being fitted and coupled without a separation distance, but a separation distance can be formed for tolerance.

As described above, the front surface of the circuit board 150 and the rear surface of the upper housing 110 can be coupled with a certain tolerance distance to prevent distortion of the circuit board 150, and to be applied as a buffer for an error in the process to reduce the defect rate.

In addition, even if the separation distance for such a tolerance is included, the circuit board 150 and the housing 110, 120 can be clearly coupled by combining with the upper and lower housings 110 and 120 by a plurality of coupling grooves and coupling holes.

Accordingly, the circuit board 150 is firstly fixed while the step 117 of the rear surface of the accommodating portion 119 and the sensor opening 115 of the circuit board 150 are fitted, and is secondarily fixed while the fixing protrusion 127 of the lower housing 120 and the protrusion hole 154 of the circuit board 150 are coupled, so that the position is specified.

Meanwhile, a sealing part 130 can be further formed between the upper housing 110 and the sensor area 540. The sealing part 130 can be elastic, and formed of a rubber, fluorinated rubber, silicon, neoprene, nitrile, polyvinyl chloride (PVC), thermoplastic polyurethane, polytetrafluorethylene and the like.

The sealing part 130 is formed as a separate element as shown in FIG. 6, and is coupled and compressed at the time of the housing 110, 120 coupling, thereby preventing the specimen from flowing to the outside of the sensor area 540.

In this case, the sealing part 130 can have a sealing opening 131 having a diameter w3 larger than the diameter w2 of the rear opening of the accommodating portion 119 as shown in FIG. 7, and the rear opening and the sealing opening 131 can be disposed to have a concentric circle. Accordingly, when assembling, as shown in FIG. 7, the sealing part 130 is disposed outside the lower opening of the accommodating portion 119 to form a concave groove.

This is designed to avoid danger that the elastic sealing part 130 is pushed to the sensor area 540 by the compression of the sealing part 130 and covers the sensor area 540 in contact with the specimen, as a tolerance is set when the sealing part 130 is compressed.

As described above, it is possible to ensure the sealing of the specimen while securing the area of the sensor area 540 by adjusting the size of the sealing opening 131 of the sealing part 130 and the opening size of the accommodating portion 119.

Meanwhile, the sealing part 130 can be a closed cell type waterproof pad having elasticity, but is not limited thereto.

Meanwhile, the connection pad 158 formed on the rear surface of the circuit board 150 is formed in the same number as the pad 511 of the sensor chip 500, and a connecting member 140 is disposed for electrical and physical connection between the connection pad 158 of the circuit board 150 and the pad 511 of the sensor chip 500.

As shown in FIG. 6, the connecting member 140 can be formed separately for each pad 158, and can be formed as a clip-type elastic contact piece. Such a connecting member 140 can be a C-clip or a spring terminal.

Each connecting member 140 can include a first surface in contact with the pad area 510 of the circuit board 150 and a second surface configured to be elastically deformable by being bent in the length direction of the first surface from one side surface of the first surface.

The first surface is formed to have a certain length and is in contact with the pad area 510 of the circuit board 150, and the second surface is in contact with the pad 511 of the lower sensor chip 500 and elastically deformed.

To this end, in the state where the connection pad 158 of the circuit board 150 and the first surface are in contact with each other through welding or soldering, when the circuit board 150 is disposed in the lower housing 120 in which the sensor chip 500 is disposed, a bending portion is elastically deformed as pressure is applied vertically (e.g., substantially vertically) to the connecting member 140 by assembling the upper housing 110 and the lower housing 120.

At this time, the angle is changed so that the second surface is parallel to the first surface as a spring coupling portion is pushed into the inside of the second surface. Thus, the second surface is in contact with the pad 510 of the sensor chip 500 to maintain a conducting state, so that physical coupling and electrical coupling occur simultaneously.

As described above, since the probe material in the sensor chip 500 is not exposed to high temperature in a bonding process by performing electrical connection of the sensor chip 500 with the circuit board 150 without a separate bonding process, it is possible to prevent a problem that protein modification occurs.

That is, in the presence of probe material vulnerable to heat due to the characteristics of the biosensor, the characteristics of the probe material can be maintained by excluding a heating process, and electrical connection between the sensor chip 500 and the circuit board 150 becomes possible.

Meanwhile, on the rear surface 129 (see FIG. 5B) of the lower housing 120 of the biosensor cartridge 100, i.e., the rear surface 129 of the cartridge 100 exposed to the outside, a QR label 160 including a QR code in which sensor information including a product ID and a manufacturing serial number for genuine product certification of the biosensor cartridge 100 is stored is attached.

The QR code can be attached to the central area of the rear surface 129 of the lower housing 120 so that the rear surface 129 of the lower housing 120 of the cartridge 100 can be aligned over the second opening 293 which is the QR opening when the cartridge 100 is coupled with the external diagnostic device 200.

The QR code can include all sensor information for genuine product certification. As an example, it can include sensor chip 500 information and cartridge information as well as the product ID and manufacturing serial number. The information of the sensor chip 500 can include probe material activated in the sensor chip 500, a disease to be diagnosed, a manufacturing date, a manufacturing location, and a manufacturing serial number of the sensor chip 500. In addition, the cartridge information can include an assembly date, a test date, and a sensor ID of the biosensor cartridge 100.

The stored QR code is read from the QR reading module 271 of the diagnostic device 200 at the same time when it is inserted into the diagnostic device 200, and a process for genuine product certification can be performed with the cloud server 400.

The biosensor cannot determine whether it is an imitation or not. Even if it is genuine, sensor errors are often found or decided from accumulated test data after manufacturing and sales. Therefore, a process of classifying the biosensor cartridge 100 in which an error has occurred is required before the test proceeds.

In the case of the biosensor cartridge 100, it is possible to check an error including a current risk to a corresponding type of the biosensor cartridge 100 through such a certification procedure.

The biosensor cartridge 100 according to the present embodiment does not include a separate memory chip for storing sensor-specific information for such a certification procedure.

When such a memory chip is separately included, the size of the circuit board 150 increases, and the size of the housing 110, 120 increases according to the size of the circuit board 150. In addition, as the circuit of the circuit board 150 becomes complicated, the number of pins used in the connection terminal 153 increases, thereby causing problems in miniaturization and cost of the cartridge 100.

Like the biosensor cartridge 100 according to the present embodiment, by attaching a QR label 160 on which a QR code is printed to the rear surface of the housing, such a memory chip can be replaced (e.g., a memory chip is not necessary), and the time difference between reading of the sensor result and certification can be minimized by reading the QR code almost simultaneously (e.g., simultaneously) with the coupling of the cartridge 100 and the diagnostic device 200.

Such a QR code can be prevented from being arbitrarily attached and detached by attaching it as a security label 160 such as a VOID label on the rear surface of the lower housing 120.

In such a biosensor cartridge 100, in a state in which the sensor chip 500 is placed in the lower housing 120, the upper housing 110 coupled to the circuit board 150 to which the connecting member 140 is attached is pressed for assembling with the lower housing 120, so that the sensor chip 500 and the circuit board 150 are physically and electrically attached and fixed.

In this case, the attachment of the upper housing 110 and the lower housing 120 can be further strengthened by performing fusion on an edge attachment area of the upper housing 110 and the lower housing 120.

Such fusion can be performed by ultrasonic fusion, but is not limited thereto, and can be performed through a separate adhesive member.

The edge attachment area formed as described above is continuously formed in the entire edge excluding an open portion through which the connection terminal 153 protrudes, i.e., in the distal end of the side surfaces of the upper housing 110 and the lower housing 120, thereby preventing moisture or foreign substances from penetrating into the interior from the outside.

Figure 13:
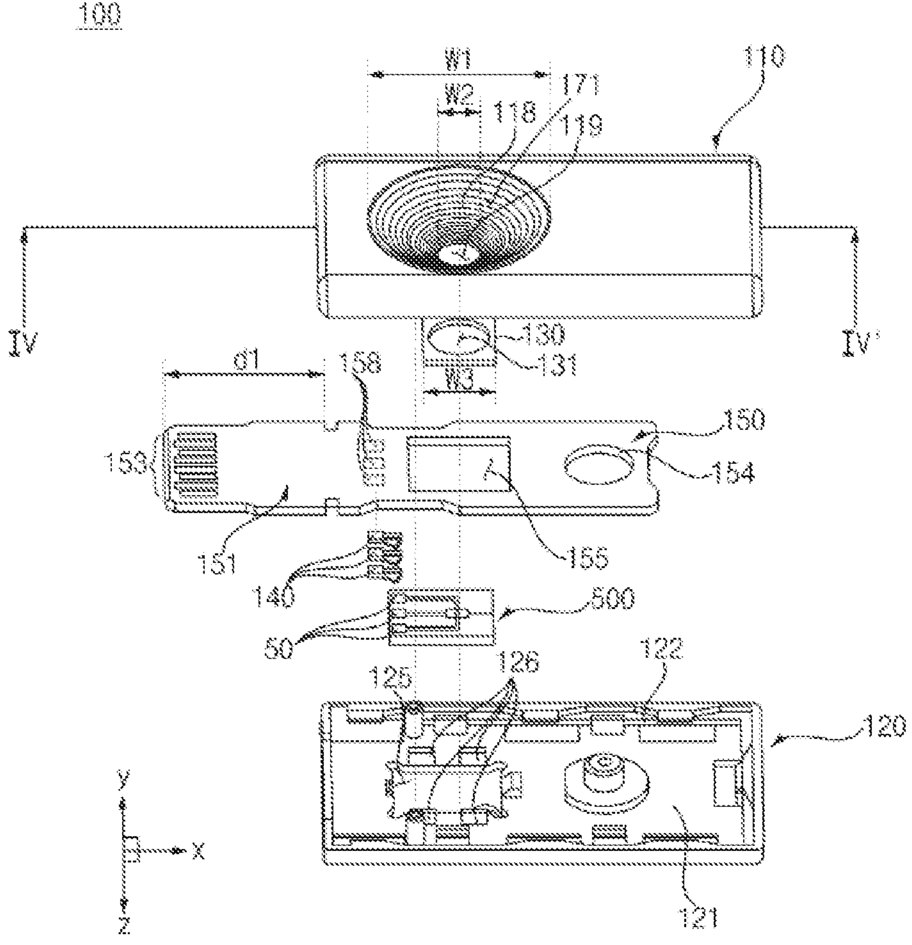
FIG. 13 is an exploded perspective view of another example of the biosensor cartridge of FIG. 1.
Figure 14:
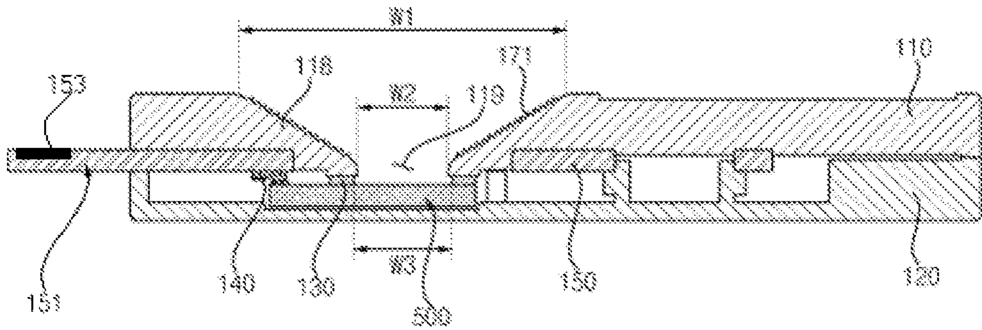
FIG. 14 illustrates the sensor chip of FIG. 13 taken along IV-IV' of FIG. 13.

Such a biosensor cartridge 100 can be changed to a configuration shown in FIGS. 13 and 14.

The biosensor cartridge 100 according to the second embodiment can be configured as shown in FIGS. 13 and 14.

FIG. 13 is an exploded perspective view of another example of the biosensor cartridge 100 of FIG. 1, and FIG. 14 illustrates the sensor chip of FIG. 13 taken along IV-IV', In the biosensor cartridge 100 of FIGS. 13 and 14, since the configuration of the lower housing 120, the sensor chip 500, and the circuit board 150 is the same as that of the biosensor cartridge 100 of FIGS. 6 and 7, and the attachment configuration of the upper housing 110 and the lower housing 120 is also the same, a description thereof is omitted.

In the biosensor cartridge 100 of the second embodiment, the accommodating portion 119 can be formed differently from the first embodiment.

Referring to FIGS. 13 and 14, in the biosensor cartridge 100 according to the second embodiment, the accommodating portion 119 for accommodating the specimen in the upper housing 110 and guiding it to the sensor area of the lower sensor chip 500 is formed.

Specifically, the accommodating portion 119 is a space for inducing a reaction with the exposed sensor area 540 by accommodating a test target specimen in a fluid state, e.g., in a liquid state, and the accommodating portion 119 is concavely recessed from the upper surface to form a conical passage, i.e., a channel, the diameter of which becomes narrower as it approaches the sensor area 540.

Accordingly, the accommodating portion 119 is formed to have an inclined surface 118 such that the diameter W1 of the opening of the upper surface is larger than the diameter of the opening W2 at the distal end of the accommodating portion 119.

In the accommodating portion 119, since the diameter W1 of the opening of the upper surface is expanded to be wider than the area of the sensor chip 500, the difference between the diameter W1 of the opening of the upper surface and the diameter W2 of the opening at the distal end of the accommodating portion 119 is significantly large. Accordingly, the accommodation volume can be maintained while the angle of the accommodating portion 119 satisfies 50 degrees or smaller.

For example, the diameter W1 of the opening of the upper surface can satisfy two to three times the diameter W2 of the opening at the distal end of the accommodating portion 119.

As the difference between the diameter W1 of the opening in the upper surface and the diameter W2 of the opening at the distal end of the accommodating portion 119 becomes larger, the accommodating volume of the accommodating portion 119 increases, so that a large amount of specimen can be accommodated.

At this time, the inclination angle of the inclined surface 118—the angle of the inclined surface with respect to the horizontal direction in which the sensor chip 500 is placed when viewed from the cross section in FIG. 9—can be uniform, but can have an inflection point.

That is, the inclination angle increases as it approaches the sensor area 540, it forms a verticality in the outermost area closest to the sensor area 540, so that it can be changed to a cylindrical passageway.

As described above, since the accommodating portion 119 has the inclined surface 118, a concave groove having a depth that is a height from the upper surface of the upper housing 110 to the channel area is formed. A specimen is collected in the groove to induce a reaction with the probe material in the sensor area 540.

As described above, the biosensor cartridge 100 accommodates the biosensor chip 500 inside the housing 110, 120, and is provided to accommodate the circuit board 150 for transmitting the detection information of the sensor chip 500 to the external diagnostic device 200.

The hyper water-repellent pattern structure shown in FIG. 8 to FIG. 12C described above is also applied to the inclined surface 118 shown in FIGS. 13 and 14, and the description is the same and omitted.

Hereinafter, the biosensor chip 500 of the present embodiment will be described with reference to FIGS. 15 to 18.

Figure 15:
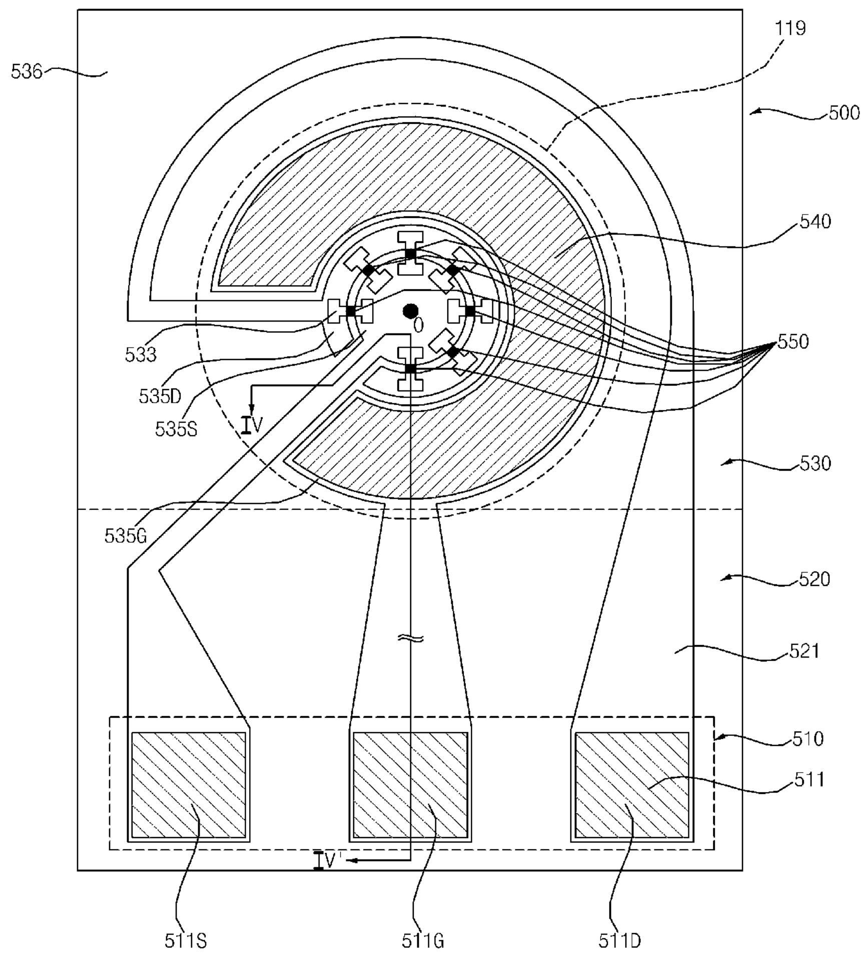
FIG. 15 is a top view of an example of a sensor chip applicable to the biosensor cartridge of FIGS. 1 to 14.
Figure 16:
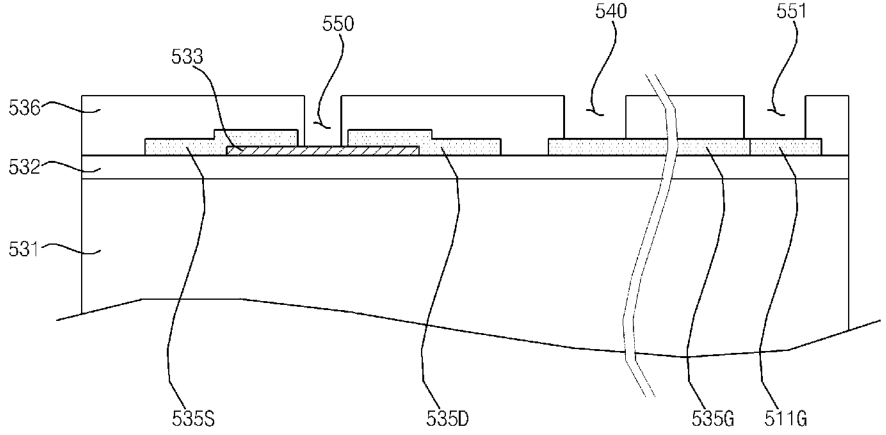
FIG. 16 illustrates the sensor chip of FIG. 15 taken along V-V'.
Figure 17A:
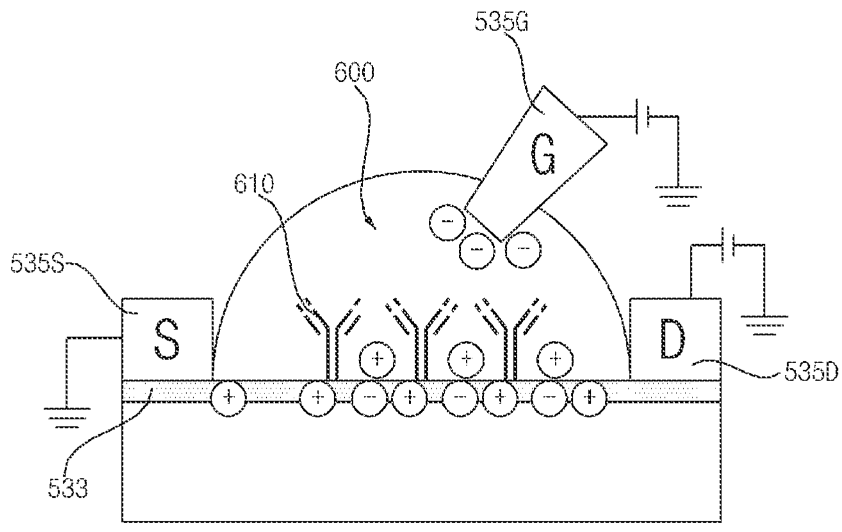
FIG. 17A and FIG. 17B are schematic diagram illustrating a reaction according to a target material of the sensor chip shown in FIG. 15.
Figure 17B:
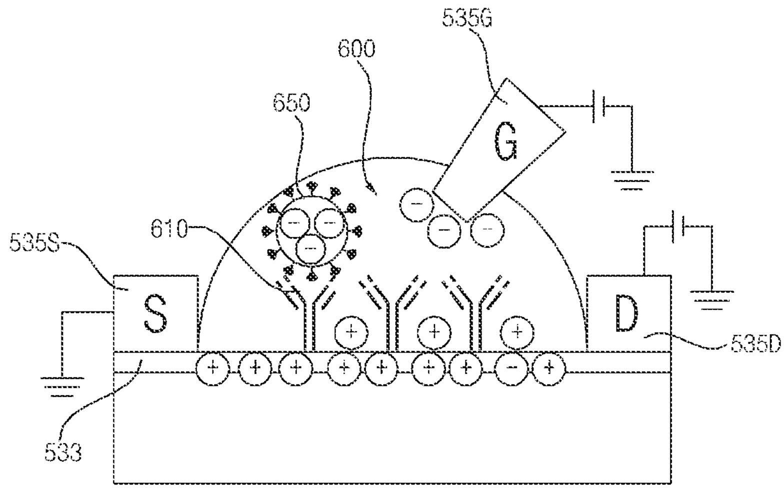
Figure 18:
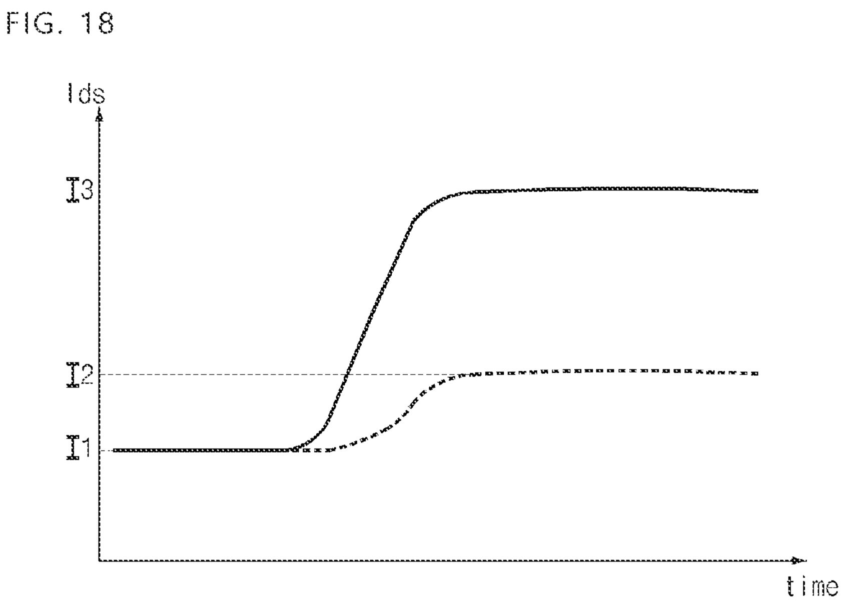
FIG. 18 is a graph illustrating changes of the output current of the sensor chip 500 according to FIG. 17A and FIG. 17B.

FIG. 15 is a top view of an example of a sensor chip applicable to the biosensor cartridge of FIGS. 6 to 13, FIG. 16 illustrates the sensor chip of FIG. 15 taken along V-V', FIG. 17A and FIG. 17B are schematic diagram illustrating a reaction according to a target material of the sensor chip 500 shown in FIG. 15, and FIG. 18 is a graph illustrating changes of the output current of the sensor chip 500 according to FIG. 16A and FIG. 16B.

The biosensor chip 500 detects a target material from a specimen introduced into the inside by the accommodating portion 119 of the biosensor cartridge 100, and transmits an electrical signal generated by reacting with the detected target material to the pad 158 of the circuit board 150 through the electrode pad 511.

For example, the specimen can refer to saliva, a body fluid including sweat, blood, a solution diluted with serum or plasma, and the like, as a biological material.

The biosensor chip 500 is a semiconductor-based sensor chip 500, and can be manufactured as a biosensor chip 500 to which graphene is applied.

The sensor chip 500 can have various sizes depending on a size of the target material, the number of the target materials, and the size of the cartridge 100, and can be designed with a size of 6*6 mm or 6*8 mm, for example.

Referring to FIG. 15 and FIG. 16, the biosensor chip 500 according to the embodiment can have a plane of rectangular shape, a sensor area 540 exposed to exterior through the accommodating portion 119 in the front surface is formed, and can be divided into the pad area 510 connected to the pad 158 of the circuit substrate 150 through the connecting member 140, which is spaced from the sensor area 540, and a connection portion 530 that connects the sensor area 540 and the pad area 510. The sensor area 540 detects a target material from the contacted specimen, and probe material that react with the target material to generate an electrical signal, e.g., an antigen, an antibody, an enzyme, and the like are attached thereto.

When the sensor area 540 comes into contact with a specimen, it interacts with a target material included in the specimen to generate an electrical signal. Accordingly, the external diagnostic device 200 connected to the biosensor 100 can analyze an electrical signal generated from the biosensor 100 to detect the presence or concentration of the target material.

The sensor area 540 includes a transistor structure, and has a structure where probe material is attached to a channel area 550 of the transistor.

Specifically, the sensor area 540 includes a plurality of circular or ring-shaped electrodes 535S (source electrode), 535D (drain electrode), and 535G (gate electrode) forming a concentric circle, and a plurality of channel areas 550 are between the plurality of electrodes 535S, 535D, and 535G, particularly, between the source electrode 535S and the drain electrode 535D.

An insulating layer 532 is formed on the semiconductor substrate 531, and the insulating layer 532 can be formed of oxide or nitride. When the semiconductor substrate 531 is a silicon substrate, the insulating layer 532 can be formed of silicon oxide or silicon nitride, and can be formed by various methods. For example, a silicon oxide layer can be formed on the surface through heat treatment.

A plurality of channels 533 are formed on the insulating layer 532 to be spaced apart from each other.

A plurality of channels 533 are disposed spaced apart by a certain distance from the center O of the sensor area 540, and a central area of each channel 533 is exposed to form the channel area 550.

That is, the plurality of channels 533 are disposed to be spaced apart from each other on the circumference of an imaginary circle having a certain length as a radius in the center O of the circle.

The plurality of channels 533 can be disposed to be spaced apart by the same angle. For example, as shown in FIG. 15, seven channels 533 can be formed, and each channel 533 can be spaced apart at an angle of 45 degrees.

Alternatively, five channels 533 can be disposed so that each channel 533 can be spaced apart at an angle of 60 degrees. However, the channels 533 can be spaced apart by any angle.

One channel 533 can be patterned in a specific shape, and can be formed of a semiconductor material. Alternatively, one channel 533 can be formed of a graphene based material that is highly reactive as a highly conductive material.

The shape of one channel 533 includes areas overlapping with the source electrode 535S and the drain electrode 535D, and a channel area 550 exposed to the outside through the accommodating portion 119 in the two overlapping areas.

As shown in FIG. 15, the channel area 550 has the channel 533 formed with an I-shape to have a width smaller than the overlapping area to have smaller resistance in the channel area 550, but not limited thereto, and can be formed with a bar type to have the same width throughout the overlapping area to the channel 533.

The source electrode 535S having the shape of a circle having the smallest diameter can be formed on the center O of the sensor area 540, and is formed to overlap with an end part of the channel 533, and overlaps with the plurality of channels 533 to simultaneously transmit the source voltage to the plurality of channels 533.

Meanwhile, a drain electrode 535D can be formed on the outer periphery of the channel area 550 to be spaced apart from the source electrode 535S.

The drain electrode 535D can be formed in a ring shape, and is formed along the circumference of an imaginary circle that surrounds the channel area 550 and has a greater diameter than that of the channel area 550.

The drain electrode 535D also simultaneously overlaps with the drain overlapping area 552 of the plurality of channels 533 to simultaneously receive current from the plurality of channels 533.

An end portion of the drain electrode 535D is cut off and forms a passage through which the connection portion 521 of the source electrode 535D passes.

Meanwhile, a gate electrode 535G is formed along the circumference of an imaginary circle having a larger diameter surrounding the drain electrode 535D.

The gate electrode 535G has the largest area and can occupy ½ to ⅔ of the sensor area 540. The gate electrode 535G is formed to be spaced apart from the source electrode, the gate electrode 535S, 535D, and the channel area 550. One end of the gate electrode 535G is disconnected to also form a channel so that the connection portion 521 of the drain electrode and the source electrode 535S, 535D is connected to the pad(s) 511. Specifically, the source electrode 535S is electrically connected to a source pad 511S, the drain electrode 535D is electrically connected to the drain pad 511D and the gate electrode 535G is connected to the gate pad 511G.

An end portion of the drain electrode 535D is also cut off and forms a passage through which the connection portion 521 of the drain electrode 535D and the source electrode 535S passes.

The electrodes 535S, 535D, and 535G of the sensor area 540 designed as shown in FIG. 15 are formed in the same layer.

Accordingly, the source electrode, the drain electrode, and the gate electrodes 535S, 535D, and 535G are all formed in the same layer and formed in one process.

For example, the source electrode, the drain electrode, and the gate electrode 535S, 535D, and 535G can be respectively formed by forming an electrode layer and simultaneously patterning a corresponding electrode layer.

Thus, a process step can be reduced, and a process time and cost can be reduced by simultaneously forming three electrodes 535S, 535D, and 535G that do not overlap each other.

The metal layer can be formed of at least one of Ni, Zn, Pd, Ag, Cd, Pt, Ga, In, and Au, but is not limited thereto.

A passivation layer 536 is formed on the electrodes 535S, 535D, and 535G.

The passivation layer 536 is formed on the entire sensor chip 500 to protect the sensor area 540 and the electrodes 535S, 535D, and 535G.

The passivation layer 536 can be formed of a material resistant to moisture, and can be formed of, for example, an oxide layer, a nitride layer, or a carbide layer.

In addition, the passivation layer 536 can be applied with a polymer resin, but is not limited thereto.

The passivation layer 536 exposes only the upper portion 551 of the plurality of channel areas 550, the gate electrode 540, and the plurality of pads 511 in the sensor chip 500, and covers all other areas.

Accordingly, the area exposed by the passivation layer 536 is very limited.

In particular, in the sensor area 540, only the gate electrode 535G and the channel area 550 are exposed to induce a reaction by directly contacting the specimen.

In the pad area 510, each pad 511S, 511D, 511G is exposed in an insulated state, and electrically in contact with each pad 158 of the circuit board 150 through a connecting member through an upper connecting member 140.

As shown in FIG. 17A, probe material 610 is attached to each of the channel areas 550 exposed as described above to activate the sensor.

The probe material 610 is a material that reacts specifically to a target material to be detected by the sensor. When the target material is an antigen, an antibody can be attached thereto, or when the target material is an antibody, an antigen can be attached thereto.

When the channel 533 is formed of graphene, a linker material (not shown) can be attached for smooth connection between the probe material 610 and graphene, and a process of attaching the probe material 610 after attaching a linker material on graphene is defined as an activation process.

The linker material is different depending on the material constituting the channel 533 and the probe material 610, and in the case of graphene, it can be a polymer structure having a nano size, for example, can be formed of at least one of polyurethane, polydimethylsiloxane, Norland Optical Adhesives NOA, epoxy, polyethylene terephthalate, polymethyl methacrylate, polyimide, polystyrene, polyethylene naphtharate, polycarbonate, and combinations thereof.

In addition, the linker material can be formed of a combination of polyurethane and NOA (e.g., NOA 68). However, the linker material is not limited thereto, and can be made of various polymers having flexibility.

FIGS. 17A and 17B are schematic diagrams illustrating a reaction of the sensor chip 500.

When the target material does not exist in the specimen as shown in FIG. 17A, the source electrode 535S receives a source voltage and the gate electrode 535G receives a gate voltage by the voltage applied to each pad 511.

The gate electrode 535G is exposed to the accommodating portion 119 and comes into contact with the specimen provided from the outside to apply a bias voltage to the specimen. Therefore, the specimen exists in a state of being partially charged with respect to the voltage of the gate electrode 535G.

At this time, the drain current Ids read from the drain electrode 535D is as shown in FIG. 17.

That is, when there is no target material reacting with the probe material 610 in the specimen 600, the drain current Ids has a first value I1, which is defined as a reference current.

At this time, as shown in FIG. 17B, when the target material 650 exists in the specimen 600, the channel 533 is charged with a specific carrier as the target material 650 reacts with the probe material 610. For example, as shown in FIG. 17B, a depletion state in which charges are accumulated in the channel 533 can proceed.

Accordingly, as the drain current Ids read from the drain electrode 535D increases, it has a second value I2 of FIG. 18.

At this time, the amount of accumulated charge is proportional to the area of the channel 533. Thus, when the number of channel 533 is one, the drain current Ids has a second value I2. When the number of channels 533 is two or more, the drain current Ids has a third value I3 greater than the second value I2. When the number of channels 533 is three or more, the drain current Ids has a fourth value I4 greater than the third value I2. Accordingly, the value of the drain current Ids read from the drain electrode 535D is amplified.

At this time, even when one channel 533 does not operate as the plurality of channels 533 are spaced apart from each other, the existence of the target material can be recognized by causing the drain current Ids to increase or decrease in other channel 533.

As described above, the graphene channel sensor chip 500 has a multi-channel structure having a plurality of channels spaced apart from each other, thereby amplifying a drain current and compensating for a malfunctioning channel.

In such a sensor chip 500, both the gate electrode 535G and the channel area 550 can be exposed by the distal end opening of the accommodating portion 119 having a circle larger than the circumference of the gate electrode 535G.

In addition, the plurality of channel areas 550 are formed to be spaced apart at the same angle and at the same distance from the center O of the sensor area 540 opened by the accommodating portion 119 such that the specimen is uniformly contacted, and formed in a shape surrounding the source and drain electrodes 535S and 535D in order to dispose the channel 533 between the source and drain electrodes 535S and 535D, thereby optimizing a structure.

In FIG. 15, the connection portion 521 is respectively included, which is connected from an end of each of the electrodes 535S, 535D, and 535G to the pad 511, and each connection portion 521 is formed of the same metal layer as the electrodes 535S, 535D, and 535G, and not overlapped with each other.

FIG. 15 shows that the pads 511 are formed in serial at an end of the sensor chip 500, but not limited thereto.

The design of the sensor chip 500 can be variously changed so long as the transistor in which the gate electrode 535G and the plurality of channels 533 are exposed is maintained in the accommodating portion 119.

Accordingly, the position of the pad 511 can also be variously changed. However, the positions of the connecting member 140 and the connection pad 158 of the circuit board 150 are also changed according to the change in the position of the pad 511.

As such, the biosensor cartridge 100 that accommodates the graphene based multi-channel sensor chip 500 and the biosensor diagnostic device 200 coupled therewith form a single biosensor system environment.

Figure 19:
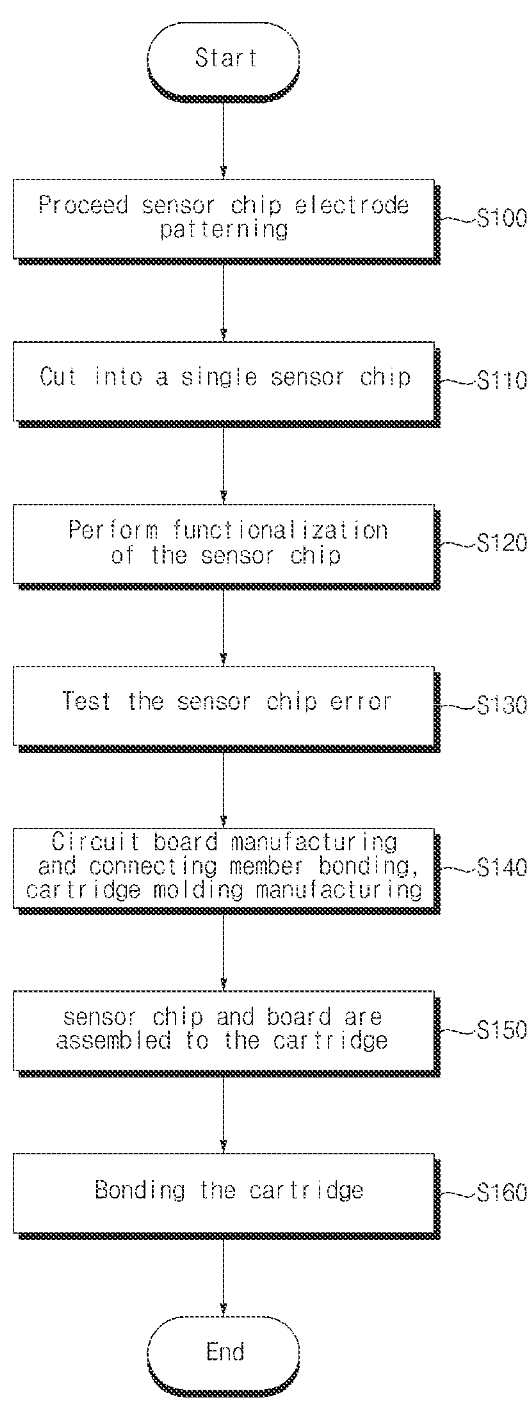
FIG. 19 is a flowchart illustrating a manufacturing process of the biosensor cartridge shown in FIG. 5.

The biosensor cartridge 100 accommodating the graphene-based multi-channel sensor chip 500 is manufactured through the process shown in FIG. 19.

Hereinafter, a method of manufacturing a biosensor cartridge including the graphene-based multi-channel sensor chip 500 of the present specification will be described with reference to FIG. 19.

Referring to FIG. 19, firstly, channel patterning of the sensor chip 500 for manufacturing the sensor chip 500 is performed on a semiconductor wafer (S100).

The manufacturing of the sensor chip 500 is a process for manufacturing the sensor chip 500 of FIGS. 15 and 16, and an insulating layer 532 made of oxide or nitride is formed on the semiconductor substrate 530.

When the semiconductor substrate 530 is a silicon substrate, the insulating layer 532 can be formed of silicon oxide or silicon nitride, and can be formed by various methods. For example, a silicon oxide layer can be formed on the surface through heat treatment.

A plurality of channels 533 are formed on the insulating layer 532 to be spaced apart from each other.

In this case, one semiconductor wafer is designed to simultaneously manufacture a plurality of unit sensor chips 500, and can perform channel patterning for manufacturing the plurality of unit sensor chips 500.

A channel layer is patterned with a plurality of channels 550 designed for each unit sensor chip 500.

For example, when the plurality of channels 550 are formed of graphene, graphene is stacked on the insulating layer and then graphene is patterned to form a plurality of channels 550 spaced apart from each other in the area of the unit sensor chip 500.

Next, electrode patterning for forming electrode and pad as shown in FIGS. 10 to 18 is performed. At least one metal layer among Ni, Zn, Pd, Ag, Cd, Pt, Ga, In, and Au for forming the electrode 535S, 535D, 535G is stacked, and the metal layer is patterned to simultaneously form the source electrode, the drain electrode, and the gate electrode 535S, 535D, 535G, the pad 511 connected to each electrode, and the connection portion 521 for connecting them. The passivation layer 536 is formed on the electrode 535S, 535D, and 535G, and patterning is performed to expose only the plurality of channel areas 550, the gate electrode 540, and the plurality of pads 511. Specifically, a source electrode 535S is electrically connected to a source pad 511S, the drain electrode 535D is electrically connected to the drain pad 511D and the gate electrode 535G is connected to the gate pad 511G.

When a plurality of unit sensor chips 500 are generated on one semiconductor wafer as described above, a cutting process of cutting the plurality of unit sensor chips 500 into a single sensor chip 500 is performed (S110).

The cutting process can be performed by laser scribing, and laser scribing can be performed together with a physical cutting process.

A single sensor chip 500 cut into a unit sensor chip 500 is defined as the sensor chip 500 of FIG. 14, and functionalization of the sensor chip 500 is performed (S120).

The functionalization of the sensor chip 500 is defined as a process of attaching probe material that performs a specific reaction to a target material to be detected by each sensor to an exposed channel area of each sensor chip 500.

For the functionalization of the sensor chip 500, when the channel 533 is formed of graphene, a linker material can be attached for a smooth connection between the probe material 610 and graphene, a process of attaching the probe material 610 after attaching the linker material on the graphene is performed.

The linker material is different depending on the material constituting the channel 533 and the probe material 610, and in the case of graphene, it can be a polymer structure having a nano size, for example, can be formed of at least one of polyurethane, polydimethylsiloxane, Norland Optical Adhesives NOA, epoxy, polyethylene terephthalate, polymethyl methacrylate, polyimide, polystyrene, polyethylene naphtharate, polycarbonate, and combinations thereof.

In addition, the linker material can be formed of a combination of polyurethane and NOA (e.g., NOA 68). However, the linker material is not limited thereto, and can be made of various polymers having flexibility.

When the functionalization of the sensor chip 500 is completed, a test process of the sensor chip 500 is performed (S130).

In the test of the sensor chip 500, the sensor chip 500 is injected into a test equipment and the test equipment is connected to the exposed pad 511, so that the alignment and electrical signals of the pad 511 are read to measure a resistance.

Thus, a physical test on whether patterning is performed accurately according to a design and a functional test on whether electrical connection is performed can be simultaneously performed.

In addition, the basic resistance value of each sensor chip 500 is received, and a failure can be determined according to whether a corresponding basic resistance value is within a certain range.

When such an error check is finished, the failure sensor chip is classified and only the sensor chip 500 that passed the check can be used as a valid chip.

Meanwhile, the circuit board 150 can be manufactured through a separate process (S140). As described above, in the circuit board 150, a base member, which is the base material of the circuit board 150, is cut and punched according to the design of the circuit board 150, and a circuit pattern is formed in one side of the base member to complete the circuit board 150.

In this case, one side of the circuit board 150 is disposed as a rear surface, and the connection pad 158, which is a part of the circuit pattern, is exposed on the rear surface.

The connecting members 140 are respectively attached to the exposed connection pad 158 according to a preset number (S150).

The bonding of the pad 158 and a first surface of the connecting member 140 can be performed by soldering so as to simultaneously satisfy the electrical and physical attachment. Accordingly, a second surface of the connecting member 140 is maintained as a free end.

Meanwhile, the upper housing 110 and the lower housing 120 can be manufactured through a separate process.

Meanwhile, the upper housing 110 and the lower housing 120 can be manufactured through a separate molding process. In this case, in molding the upper housing 110, the molding can be manufactured to form the hyper water-repellent pattern structure 171 on the inclined surface of the accommodating portion 119 of the upper housing 110.

As described above, when the molding is removed in a vertical direction after resin material such as polycarbonate is injected into the mold, the upper housing in which the hyper water-repellent pattern structure 171 is manufactured.

Accordingly, the hyper water-repellent pattern structure 171 can be formed by a single injection without a separate laser ablation, and additionally, the hyper water-repellent coating surface 170 can be selectively formed on the accommodating portion 119 of the upper housing 110.

Next, in a state in which the sensor chip 500 is disposed in the area of the sensor chip 500 of the lower housing 120 of the cartridge 100 and the circuit board 150 is placed thereon, the upper housing 110 is pressed, so that the second surface of the connecting member 140 is fixed in a state of being bonded to the pad 511 of the sensor chip 500 (S150).

Accordingly, electrical connection and physical connection between the circuit board 150 and the sensor chip 500 are simultaneously achieved.

In such a state, the end of the lower housing 120 and the upper housing 110 of the cartridge 100 is fused with ultrasonic fusion, and a part of the resin is melt, and then, the resin is cured, and accordingly, the cartridge 100 is integrated (S160). By the fusion process, the upper housing 110 and the lower housing 120 are in an inseparable state, and the manufacture is completed.

Through such a manufacturing process, failure of the sensor chip 500 is firstly filtered and then assembling is performed. In the assembling step, a high-temperature process by wire bonding is not applied, so that the functionalized sensor chip 500 is prevented from being deteriorated due to heat.

In addition, since a process for protecting a device by performing plastic molding is not added after wire bonding of the sensor chip 500, deterioration of the probe material of the sensor chip 500 due to high temperature is prevented.

Figure 20:
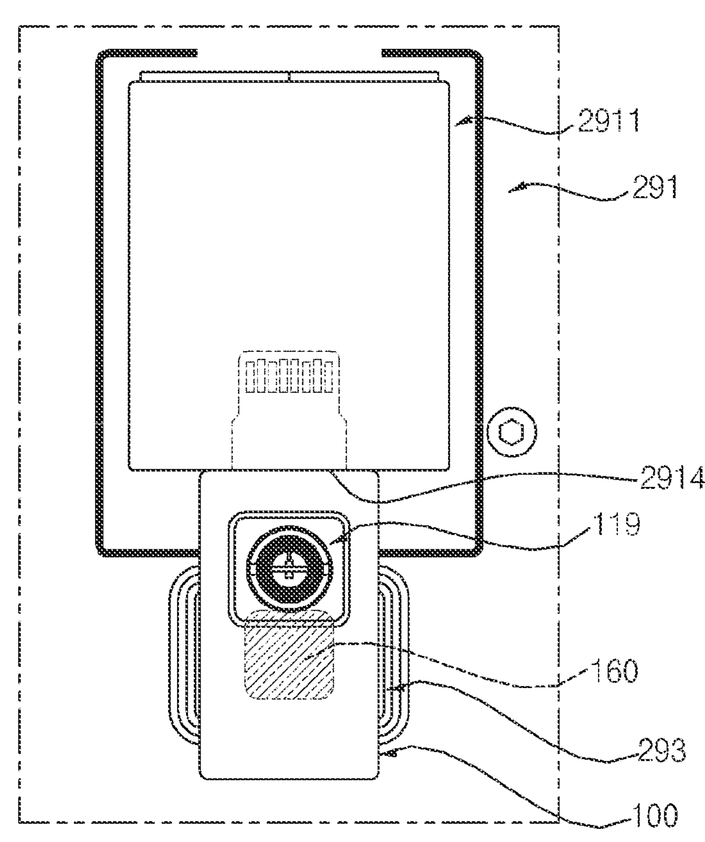
FIG. 20 is a coupling diagram in which the biosensor cartridge is coupled to the biosensor diagnostic device in the biosensor system of FIG. 1.

The biosensor cartridge 100 accommodating the graphene-based multi-channel sensor chip 500 manufactured as described above performs the certification of the sensor cartridge 100 and the diagnosis of the specimen by inserting the connection terminal 153 of the cartridge into the insertion hole 2914 of the insertion module 2911 of the diagnostic device of FIG. 2 as shown in FIG. 20.

FIG. 20 is a coupling diagram in which the biosensor cartridge 100 is coupled to the biosensor diagnostic device 200 in the biosensor system of FIG. 1.

As shown in FIG. 20, when a test target specimen is received in the accommodating portion 119 of the biosensor cartridge 100 in the biosensor system according to the present embodiment, the connection terminal 153 of the biosensor cartridge 100 is inserted into the insertion hole 2914 of the cartridge insertion module 2911 of the biosensor diagnostic device 200.

As described above, the specimen can be a body fluid such as saliva or sweat, or blood.

When a plurality of insertion holes 2914 are disposed, the connection terminal 153 is inserted into the insertion hole 2914 of a type matching the type of the connection terminal 153.

The insertion of the cartridge connection terminal 153 can be performed in the same manner as the insertion of the USB memory as the cartridge connection terminal 153 is similar to the USB terminal.

As described above, when the biosensor cartridge 100 and the biosensor diagnostic device 200 are coupled for analysis, the state shown in FIG. 20 is maintained.

That is, the accommodating portion 119 in which the test targeting specimen is accommodated is located outside the diagnostic device 200, and transmits an electrical signal in a state in which only the connection terminal 153 is inserted into the diagnostic device 200 through the insertion hole 2914.

The rear surface 129 of the lower housing 120 of the cartridge 100 faces the front panel 291, the QR label 160 attached to the rear surface 129 of the lower housing 120 is aligned with the QR opening 293 of the front panel 291, and the QR reading module 271 is turned on so that the camera reads the QR code of the QR label 160 of the rear surface 129 of the cartridge 100 on the QR opening 293.

The operation unit 250 decodes the QR information to extract sensor information stored as QR information. In this case, the sensor information can include the sensor chip 500 type, linker information, probe material information, product ID, board ID, manufacturer information, manufacturing date, assembly date, test date, manufacturing number, and the like.

The operation unit 250 can perform a certification of the biosensor cartridge 100 by at least one cloud server 400 connectable through the wireless communication module 261.

When the biosensor cartridge 100 is genuine, the correction data is downloaded from the cloud server 400 (S60), the cartridge insertion module 2911 is driven to read the detection signal of the cartridge connection terminal 153 from the sensor controller 240, the signal conversion amplifier unit 210, and the signal filtering unit 220.

At this time, the gate voltage and the source voltage are transmitted to the cartridge 100 through the sensor controller 260, and the drain current that is changed accordingly is read from the signal conversion amplifier 210.

Such read drain current value is amplified, and digitized after noise is removed, and transmitted to the operation unit 250.

A detection signal is decoded by executing a stored algorithm with respect to the drain current value, which is the transmitted digitized detection signal, thereby reading whether the target material exists in the specimen currently accommodated in the cartridge 100.

At this time, the operation unit 250 downloads the correction data for a corresponding cartridge from the cloud server 400 after genuine product certification, and accordingly upgrades a corresponding algorithm, so that the optimized algorithm for the accumulated results of the same type of cartridge can be applied to the analysis.

The operation unit 250 reads the detection signal by performing the upgraded algorithm, and transmits the result to the display module 295 for visualization (S70).

In addition, it can operate to transmit a corresponding reading result to the cloud server 400, and transmit to a connected user terminal 300, so that a user can be notified by a designated user terminal 300.

The biosensor is not easy to determine whether it is an imitation. Even if it is genuine, sensor errors are often found from test data accumulated after manufacturing and sales. Therefore, a process of classifying the biosensor cartridge 100 in which an error has occurred is required before the test proceeds.

The biosensor system of the present embodiment can check an error including a current risk to a corresponding type of the biosensor cartridge 100 through such a certification procedure.

In addition, as the insertion of cartridge 100 and the genuine product certification are performed simultaneously, certification is performed by using a separate QR reader, and then the certified cartridge is applied to the diagnostic device 200 so that two-step operation of diagnosis can be merged into one operation. Therefore, the user's convenience is increased, and the genuine product certification of cartridge and the cartridge diagnosis are performed almost simultaneously and proceeded in a state where the cartridge inserted, so that the diagnosis result of a corresponding cartridge and the information of the cartridge are not mixed and can be clearly matched.

According to the disclosure, an optimal accommodating portion structure for injecting a test specimen to the cartridge is provided, and flow of the specimen outside can be minimized, and internal and external devices can be protected, and accordingly, inflow of the specimen to the diagnostic device can be prevented in coupling the diagnostic device.

Furthermore, a hyper water-repellent structure is applied on a surface of the specimen accommodating portion of the cartridge, the specimen is not remained on the accommodating portion, and sufficient reaction can be induced with only a small amount of the test specimen since the specimen is collected in the sensor area.

In addition, an optimal structure for the accommodating portion and the hyper water-repellent pattern by controlling an angle of the hyper water-repellent structure of the accommodating portion, the hyper water-repellent effect can be maximized.

Various embodiments described herein may be implemented in a computer-readable medium using, for example, software, hardware, or some combination thereof. For example, the embodiments described herein may be implemented within one or more of Application Specific Integrated Circuits (ASICs), Digital Signal Processors (DSPs), Digital Signal Processing Devices (DSPDs), Programmable Logic Devices (PLDs), Field Programmable Gate Arrays (FPGAs), processors, controllers, micro-controllers, microprocessors, other electronic units designed to perform the functions described herein, or a selective combination thereof. In some cases, such embodiments are implemented by the controller. For Example, the controller is a hardware-embedded processor executing the appropriate algorithms (e.g., flowcharts) for performing the described functions and thus has sufficient structure. Also, the embodiments such as procedures and functions may be implemented together with separate software modules each of which performs at least one of functions and operations. The software codes can be implemented with a software application written in any suitable programming language. Also, the software codes can be stored in the memory and executed by the controller, thus making the controller a type of special purpose controller specifically configured to carry out the described functions and algorithms. Thus, the components shown in the drawings have sufficient structure to implement the appropriate algorithms for performing the described functions.

For a software implementation, the embodiments such as procedures and functions may be implemented together with separate software modules each of which performs at least one of functions and operations. The software codes can be implemented with a software application written in any suitable programming language. Also, the software codes may be stored in the memory and executed by the controller. Thus, the components shown in the drawings have sufficient structure to implement the appropriate algorithms for performing the described functions.

The present invention encompasses various modifications to each of the examples and embodiments discussed herein. According to the invention, one or more features described above in one embodiment or example can be equally applied to another embodiment or example described above. The features of one or more embodiments or examples described above can be combined into each of the embodiments or examples described above. Any full or partial combination of one or more embodiment or examples of the invention is also part of the invention.

What is claimed is:

1. A biosensor cartridge comprising:

a circuit board including a connection terminal configured to be electrically connectable to an external diagnostic device;

a sensor chip including a reactant, the sensor chip being configured to:

detect a target material from an applied analysis specimen, react, via the reactant, with the analysis specimen to generate an electrical signal, and transmit the electrical signal generated by reacting with the detected target material to the connection terminal the circuit board; and a housing configured to accommodate the circuit board and the sensor chip so that the connection terminal is exposed, wherein the housing includes an accommodating portion for accommodating the analysis specimen, wherein the accommodating portion has an inclined surface on which the analysis specimen flows and which exposes a sensor area the sensor chip, wherein the inclined surface the accommodating portion includes a plurality of pattern grooves configured to create a contact angle between the analysis specimen and the plurality of pattern grooves which is 100 degrees or greater for lowering a surface energy the analysis specimen, and wherein the plurality of pattern grooves includes a pattern groove and a pattern protrusion, a width the pattern groove being 1.5 to 4.5 times a width the pattern protrusion.

2. The biosensor cartridge of claim 1, wherein a diameter of the accommodating portion gradually decreases from an upper surface of the housing, and wherein an end of the accommodating portion has an opening to expose the sensor area of the sensor chip.

3. The biosensor cartridge of claim 2, wherein the plurality of pattern grooves have a ring shape with different diameters, and wherein the opening of the accommodating portion is formed at a center of the accommodating portion.

4. The biosensor cartridge of claim 3, wherein each of the plurality of pattern grooves has a first width, and wherein the plurality of pattern grooves have a predetermined separation distance between respective pattern grooves.

5. The biosensor cartridge of claim 4, wherein the first width is about 1.5 to 4.5 times the predetermined separation distance.

6. The biosensor cartridge of claim 5, wherein the first width is about 100 to 250 μm, and the predetermined separation distance is about 80 to 160 μm.

7. The biosensor cartridge of claim 4, wherein a depth of each the plurality of pattern grooves is about 25 to 55 μm.

8. The biosensor cartridge of claim 4, wherein the plurality of pattern grooves formed on the inclined surface the accommodating portion has a micron size.

9. The biosensor cartridge of claim 4, wherein each the plurality of pattern grooves includes:

a bottom surface; and a side surface extending from the bottom surface, and wherein for each the plurality of pattern grooves, the side surface is inclined with respect to the bottom surface by 90 degrees or greater.

10. The biosensor cartridge of claim 9, wherein the side surface of each the plurality of pattern grooves is formed perpendicular with respect to a plane the sensor area the sensor chip.

11. The biosensor cartridge of claim 4, wherein the accommodating portion further includes a vertical surface extending from the inclined surface in a direction away from the upper surface the housing.

12. The biosensor cartridge of claim 4, wherein the plurality of pattern grooves are simultaneously formed with the housing by injection molding.

13. The biosensor cartridge of claim 7, wherein the accommodating portion further includes a coating layer for lowering a surface energy on the plurality of pattern grooves.

14. The biosensor cartridge of claim 13, wherein the coating layer is formed with fluorine-based polymer and includes one of perfluoroalkoxy alkanes (PFA), fluorine-based acrylate, methacrylate, or perfluoropolyether (PFPE).

15. The biosensor cartridge of claim 13, wherein the coating layer is formed with a thickness smaller than the depth of each the plurality of pattern grooves.

16. The biosensor cartridge of claim 1, wherein the sensor area comprises:

a substrate, a channel area in which at least one channel is formed, the channel area being on the substate, a source electrode overlapped with a first end the at least one channel;

a drain electrode overlapped with a second end the at least one channel, the drain electrode being spaced apart from the source electrode, a gate electrode spaced apart from the source electrode and the drain electrode and introducing bias voltage to the analysis specimen, and a passivation layer for covering the sensor area, the passivation layer opening only an upper portion the channel area and the gate electrode.

17. The biosensor cartridge of claim 16, wherein the housing includes an upper housing in which the accommodating portion is formed and a lower housing facing the upper housing, and wherein the upper housing and the lower housing are fused together in a state of accommodating the sensor chip and the substrate.

18. The biosensor cartridge of claim 1, wherein the accommodating portion further includes a guard protruding upwardly from an upper surface the housing and accommodating the analysis specimen.

19. The biosensor cartridge of claim 18, wherein the accommodating portion further includes a guide groove surrounding the guard on the upper surface the housing, the guide groove accommodating a portion the analysis specimen flowing from the guard.

20. A biosensor cartridge including a connection terminal exposed at a side, the connection terminal outputting an electronic detection signal generated according to a detected target material from an applied analysis specimen; and a diagnostic device including:

a display device; and an insertion hole to which the connection terminal the biosensor cartridge is inserted, wherein the diagnostic device is configured to analyze the electronic detection signal from the biosensor cartridge, determine a concentration the detected target material and display the concentration the detected target material on the display device, wherein the biosensor cartridge includes;

a sensor chip including a sensor area reacting with the detected target material;

a circuit substrate connected to the sensor chip and formed with the connection terminal at an end thereof; and a housing for accommodating the circuit substrate and the sensor chip, wherein the housing includes an accommodating portion for accommodating the analysis specimen, wherein the accommodating portion has an inclined surface on which the analysis specimen flows, and exposes the sensor area the sensor chip, and wherein the inclined surface the accommodating portion includes a plurality of pattern grooves configured to create a contact angle between the analysis specimen and the plurality of pattern grooves which is 100 degrees or greater for lowering a surface energy the analysis specimen, and wherein the plurality of pattern grooves includes a pattern groove and a pattern protrusion, a width the pattern groove being 1.5 to 4.5 times a width the pattern protrusion.

* * * * *